(12) United States Patent
Zhu et al.

(10) Patent No.: US 12,129,258 B2
(45) Date of Patent: Oct. 29, 2024

(54) DIARYL MACROCYCLIC COMPOUND AND PHARMACEUTICAL COMPOSITION, AND USE THEREOF

(71) Applicant: PrimeGene (Beijing) Co., Ltd., Beijing (CN)

(72) Inventors: Li Zhu, Beijing (CN); Wei Wu, Beijing (CN); Yanqing Yang, Beijing (CN); Wei Hu, Beijing (CN)

(73) Assignee: PRIMEGENE (BEIJING) CO., LTD, Beijing (CN)

( * ) Notice: Subject to any disclaimer, the term of this patent is extended or adjusted under 35 U.S.C. 154(b) by 1023 days.

(21) Appl. No.: 17/049,734

(22) PCT Filed: Apr. 22, 2019

(86) PCT No.: PCT/CN2019/083644
§ 371 (c)(1),
(2) Date: May 20, 2021

(87) PCT Pub. No.: WO2019/206069
PCT Pub. Date: Oct. 31, 2019

(65) Prior Publication Data
US 2022/0162218 A1    May 26, 2022

(30) Foreign Application Priority Data

Apr. 25, 2018 (CN) .......................... 201810377811.1

(51) Int. Cl.
| | | |
|---|---|---|
| C07D 487/14 | (2006.01) | |
| A61P 35/00 | (2006.01) | |
| C07D 498/22 | (2006.01) | |
| C07D 515/14 | (2006.01) | |

(52) U.S. Cl.
CPC ............ *C07D 487/14* (2013.01); *A61P 35/00* (2018.01); *C07D 498/22* (2013.01); *C07D 515/14* (2013.01)

(58) Field of Classification Search
CPC .. C07D 487/14; C07D 498/22; C07D 515/14; A61P 35/00
See application file for complete search history.

(56) References Cited

U.S. PATENT DOCUMENTS

| | | |
|---|---|---|
| 8,933,084 B2 | 1/2015 | Andrews et al. |
| 2012/0108568 A1 | 5/2012 | Allen et al. |
| 2015/0031667 A1 | 1/2015 | Allen et al. |
| 2015/0336970 A1* | 11/2015 | Andrews ............... C07D 519/00 540/456 |
| 2017/0002023 A1 | 1/2017 | Cui et al. |
| 2017/0107232 A1 | 4/2017 | Andrews et al. |
| 2017/0112842 A1 | 4/2017 | Andrews et al. |
| 2017/0114059 A1 | 4/2017 | Andrews et al. |
| 2017/0114069 A1 | 4/2017 | Allen et al. |
| 2017/0119770 A1 | 5/2017 | Allen et al. |
| 2017/0283435 A1 | 10/2017 | Andrews et al. |
| 2017/0334929 A1 | 11/2017 | Cui et al. |
| 2018/0263984 A1 | 9/2018 | Allen et al. |
| 2019/0031684 A1 | 1/2019 | Andrews et al. |
| 2019/0169207 A1 | 6/2019 | Cui et al. |
| 2019/0365763 A1 | 12/2019 | Allen et al. |

(Continued)

FOREIGN PATENT DOCUMENTS

| | | |
|---|---|---|
| AU | 2015209239 A1 | 7/2016 |
| CA | 2936079 A1 | 7/2015 |
| CN | 102971322 A | 3/2013 |

(Continued)

OTHER PUBLICATIONS

Patani et al. "Bioisosterism: A Rational Approach in Drug Design", Chem. Rev. 1996, 96, 3147-3176. (Year: 1996).*
Extended European Search Report dated May 11, 2021, issued in related EP Application No. 19791600.0, 10 pgs.
First Japanese Office Action issued on Jul. 4, 2023 for Japanese Patent Application No. 2022-100260 (4 pages).
Ries et al., "Targeting Tumor-Associated Macrophages with Anti-CSF-1R Antibody Reveals a Strategy for Cancer Therapy," copyright Jun. 2014, Cancer Cell., vol. 25, No. 6, pp. 846-859.
Bertotti et al., "Inhibition of Src Impairs the Growth of Met-Addicted Gastric Tumors," copyright 2010, Clin. Cancer Res., vol. 16, No. 15, pp. 3933-3943.
Ravi et al., "Treatment of tenosynovial giant cell tumor and pigmented villonodular synovitis," copyright 2011, Current Opinion on Oncology, Vo. 23, pp. 361-366.

(Continued)

*Primary Examiner* — Yevgeny Valenrod
(74) *Attorney, Agent, or Firm* — Fox Rothschild LLP

(57) ABSTRACT

The present invention provides a compound as represented by formula (1) or a pharmaceutically acceptable salt, a solvate, an active metabolite, a polymorph, an isotope label, an isomer or a prodrug thereof. The present invention also provides a pharmaceutical composition containing the same and the use of the compound and the pharmaceutical composition in preparation of drugs for treating tyrosine kinase-mediated diseases. The compound and the pharmaceutical composition comprising same provided by the present disclosure have significant tyrosine kinase inhibitory activity, can overcome tumor drug resistance, and break through blood-brain barrier, also have excellent pharmacokinetic properties and excellent oral bioavailability, and can be administered in a small dosage, thereby reducing treatment costs and possible side effects to a patient. Thus, the application potential is very great.

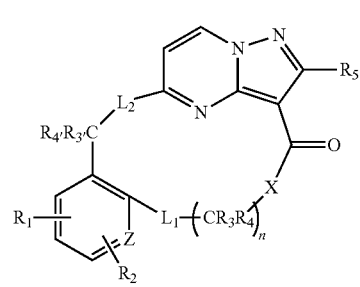

Formula (1)

7 Claims, 1 Drawing Sheet

(56) References Cited

U.S. PATENT DOCUMENTS

| | | |
|---|---|---|
| 2020/0216465 A1 | 7/2020 | Cui et al. |
| 2020/0291026 A1 | 9/2020 | Andrews et al. |

FOREIGN PATENT DOCUMENTS

| | | | |
|---|---|---|---|
| CN | 106170289 A | 11/2016 | |
| CN | 109715165 A | 5/2019 | |
| CN | 110577549 A | 12/2019 | |
| CN | 111182903 A | 5/2020 | |
| CN | 111511749 A | 8/2020 | |
| CN | 111902417 A | 11/2020 | |
| EP | 2451812 | 5/2012 | |
| EP | 2571883 | 3/2013 | |
| EP | 2918588 A1 | 9/2015 | |
| EP | 3097107 | 11/2016 | |
| EP | 3205654 A1 | 8/2017 | |
| EP | 3299372 A1 | 3/2018 | |
| EP | 3521291 A1 | 8/2019 | |
| EP | 3572416 A1 | 11/2019 | |
| EP | 3636648 A1 | 4/2020 | |
| EP | 3636649 A1 | 4/2020 | |
| EP | 3636650 A1 | 4/2020 | |
| JP | 2012532888 A | 12/2012 | |
| JP | 2013530142 A | 7/2013 | |
| JP | 2015063568 A | 4/2015 | |
| JP | 2015221834 A | 12/2015 | |
| JP | 2017503867 A | 2/2017 | |
| JP | 2017082004 A | 5/2017 | |
| JP | 2017082018 A | 5/2017 | |
| JP | 2019104748 A | 6/2019 | |
| JP | 2019104756 A | 6/2019 | |
| JP | 2021508050 A | 2/2021 | |
| JP | 2021519297 A | 8/2021 | |
| JP | 7128345 B2 | 8/2022 | |
| KR | 20160111395 A | 9/2016 | |
| TW | 201202254 A | 1/2012 | |
| TW | 201932472 A | 8/2019 | |
| WO | 2011006074 A1 | 1/2011 | |
| WO | 2011/146336 A1 | 11/2011 | |
| WO | 2015/112806 A2 | 7/2015 | |
| WO | WO-2017015367 A1 * | 1/2017 | ........... A61K 31/395 |
| WO | 2019023417 A1 | 1/2019 | |
| WO | 2019206069 A1 | 10/2019 | |
| WO | 2021063276 A1 | 4/2021 | |
| WO | 2021178296 A1 | 9/2021 | |

OTHER PUBLICATIONS

Van Tonder et al., "Preparation and Physicochemical Characterization of 5 Niclosamide Solvates and 1 Hemisolvate," copyright 2004, AAPT PharmSciTech, vol. 5, No. 1, Article 12.

Song et al., "Dual inhibition of MET and SRC kinase activity as a combined targeting strategy for colon cancer," copyright 2017, Experimental and Therapeutic Medicine, vol. 14, pp. 1357-1366.

Yang et al., "Tumor-associated macrophages: from basic research to clinical application," copyright 2017, Journal of Hematology & Oncology, vol. 10, Article No. 58.

Sawyers, "Targeted cancer therapy," copyright 2004, Nature, vol. 432, pp. 294-297.

Parsons et al., "Src family kinases, key regulators of signal transduction," copyright 2004, Oncogene, vol. 23, pp. 7906-7909.

Manning et al., "The Protein Kinase Complement of the Human Genome," copyright 2002, Science, vol. 298, pp. 1912-1934.

Chinese language International Search Report mailed on May 5, 2022 in PCT/CN2022/075712.

English translation of International Search Report mailed on May 5, 2022 in PCT/CN2022/075712.

Chinese language Written Opinion mailed on May 5, 2022 in PCT/CN2022/075712.

English translation of Written Opinion mailed on May 5, 2022 in PCT/CN2022/075712.

* cited by examiner

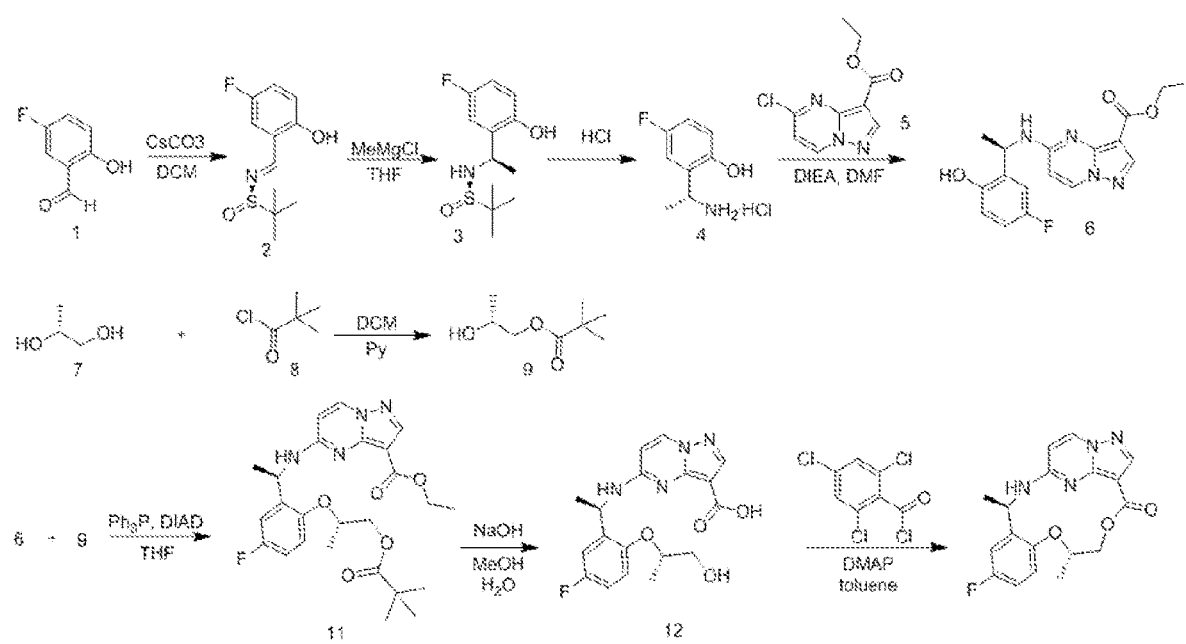

DIARYL MACROCYCLIC COMPOUND AND PHARMACEUTICAL COMPOSITION, AND USE THEREOF

CROSS REFERENCE

The application claims the priority of the Chinese invention application No. 201810377811.1 filed on Apr. 25, 2018, and the contents of the above-mentioned Chinese application are incorporated here in full as a part of this disclosure.

TECHNICAL FIELD

The present disclosure relates to the pharmaceutical field, in particular to a diaryl macrocyclic compound, a pharmaceutical composition containing the compound and use thereof.

BACKGROUND

Protein kinases are the key regulators of cell growth, proliferation and survival. Many diseases, including cancer, pain, nervous system diseases, autoimmune diseases and inflammation, are mediated by receptor tyrosine kinases such as TRK, ROS1, ALK, JAK2, SRC, FAK, FYN, LYN, YES, FGR, FAK, ARK5, AXL, and so on.

Neurotrophic tyrosine receptor kinase (NTRK), or Tropmomyosin receptor kinases (TRK), belongs to receptor tyrosine kinase family. There are three members in NTRK/TRK family, NTRK1/TRKA, NTRK2/TRKB and NTRK3/TRKC. TRK fusion proteins are closely related to tumors. Many fusion proteins, such as CD74-NTRK1, MPRIP-NTRK1, QKI-NTRK2, ETV6-NTRK3, BTB1-NTRK3 have been found in a variety of tumors, such as colon cancer, lung cancer, head and neck cancer, breast cancer, thyroid cancer, glioma and so on. Therefore, in recent years, TRK fusion protein is becoming an effective anticancer target and research hotspot. For example, WO2010048314 and WO2010033941 have disclosed TRK kinase inhibitors with different compound pregnane nucleus structure. In addition, the target mutations after continuous drug administration are important reason for tumor resistance, and many resistance NTRK mutations have been found in clinic, such as NTRK1 G595R and G667C mutations (Russo M et al. Cancer Discovery, 2016, 6 (1), 36-44), and NTRK3 G623R mutation (Drilon A. et al., Annals of Oncology, 2016, 27 (5)), 920-926). So, new-generation TRK inhibitors are expected to solve the problem of drug resistance caused by NTRK mutations.

ALK (Anaplastic lymphama kinase) inhibitors have achieved great success in the treatment of lung cancer patients with abnormal ALK genes, but the emergence of drug resistance limits the long-term clinical use of these drugs. The mechanisms of drug resistance include target gene amplification, acquired resistance mutation, activation of by-pass and downstream pathways, epithelial mesenchymal transition, tumor metastasis, or the like. None of the ALK inhibitors currently on the market may overcome drug resistance based on by-pass activation or epithelial mesenchymal transition. It is very urgent to develop new ALK inhibitors that may simultaneously overcome multi-drug resistance.

After gene rearrangement, ROS1 kinase produces constitutive active fusion proteins in a variety of cancers, such as glioblastoma, non-small cell lung cancer, cholangiocarcinoma, ovarian cancer, gastric adenocarcinoma, colorectal cancer, inflammatory myofibroblastic tumor, angiosarcoma and epithelioid hemangioendothelioma. Inhibition of ROS1 fusion protein may effectively inhibits ROS1-positive tumors. FDA has approved several new drugs for ALK positive NSCLC, but for ROS1-positive NSCLC patients, there is still not much choice except for Crizotinib which is approved for the treatment of ROS1-positive NSCLC. In addition, acquired drug resistance has emerged in clinical use of Crizotinib, and the resistance mutation sites are mainly ROS1 G2032 and ROS1 L2026M. There is also an urgent need to develop ROS 1 inhibitors for wild and resistant mutations.

EGFR inhibitors have achieved great success in the treatment of NSCLC patients, but the appearance of drug resistance is also a very tough problem. In EGFR resistant population, it was found that multiple signal pathways were over-expressed, such as MET, CDCP1, AXL, SHP2. In addition, JAK2/STAT3 and Src-YAP1 signaling pathways also affect the therapeutic effect of EGFR inhibitors. The development of multifunctional inhibitors, which may act on JAK2, Src/FAK, AXL, or the like, are expected to be combined with EGFR inhibitors to overcome the drug resistance from functional by-pass pathways.

SUMMARY

An object of the present disclosure is to provide a compound or a pharmaceutically acceptable salt, a solvate, an active metabolite, a polymorph, an isotope label, an isomer or a prodrug thereof, which has excellent activity of inhibiting tyrosine kinase.

Another object of the present disclosure is to provide a pharmaceutical composition.

Another object of the present disclosure is to provide a use of a compound or a pharmaceutically acceptable salt, a solvate, an active metabolite, a polymorph, an isotope label, an isomer or a prodrug thereof.

The present disclosure provides a compound represented by Formula (1) or a pharmaceutically acceptable salt, a solvate, an active metabolite, a polymorph, an isotope label, an isomer or a prodrug thereof,

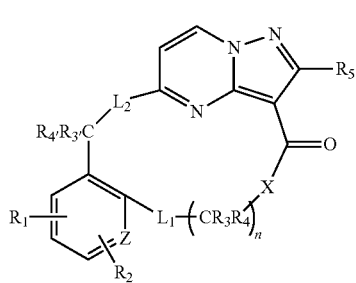

Formula (1)

wherein,

X is selected from —O—, —S— or —CR$_a$R$_b$—;

R$_a$ and R$_b$ are each independently selected from the following substituted or unsubstituted groups: hydrogen, halogen, a C$_{1~8}$ alkyl, a C$_{1~8}$ alkoxy, a C$_{1~8}$ haloalkyl, a C$_{3~8}$ cycloalkyl, a C$_{3~8}$ heterocyclyl, a C$_{6~20}$ aryl, a C$_{5~20}$ heteroaryl, hydroxyl, mercapto, carboxy, ester group, acyl, amino, amide, sulfonyl, cyano, or CR$_a$R$_b$ together forms a 3-10 membered cycloalkyl group or a 3-10 membered heterocyclic group containing at least one heteroatom;

L$_1$ is selected from —O—, —S—, —S(=O)—, —S(=O)$_2$—, —NR$_6$— or a single bond;

L$_2$ is selected from —O—, —S—, —S(=O)—, —S(=O)$_2$— or —NR$_6$—;

R$_1$, R$_2$, and R$_5$ are each independently selected from the following substituted or unsubstituted groups: hydrogen, halogen, a C$_{1~8}$ alkyl, a C$_{1~8}$ alkoxy, a C$_{1~8}$ haloalkyl, a C$_{3~8}$ cycloalkyl, a C$_{3~8}$ heterocyclic group, a C$_{6-20}$ aryl group, a C$_{5-20}$ heteroaryl group, hydroxyl, mercapto, carboxyl, ester group, acyl, amino, amide, sulfonyl or cyano;

the substituents R$_3$ and R$_4$ on each C atom are each independently selected from the following substituted or unsubstituted groups: hydrogen, halogen, a C$_{1~8}$ alkyl, a C$_{1~8}$ alkoxy, a C$_{1~8}$ haloalkyl, a C$_{3~8}$ cycloalkyl, a C$_{3~8}$ heterocyclyl, a C$_{6~20}$ aryl, a C$_{5~20}$ heteroaryl, hydroxy, mercapto, carboxy, ester group, acyl, amino, amido, sulfonyl, cyano, or the substituents R$_3$ and R$_4$ together with X group form a 3-10 membered cycloalkyl group, a 3-10 membered heterocyclic group containing at least one heteroatom, or a 5-10 membered heteroaryl group containing at least one heteroatom; or R$_3$ and R$_4$ are each independently a single bond connecting the C atom and the adjacent macrocyclic ring atom;

R$_{3'}$ and R$_{4'}$ are each independently selected from the following substituted or unsubstituted groups: hydrogen, halogen, a C$_{1~8}$ alkyl, a C$_{1~8}$ alkoxy, a C$_{1~8}$ haloalkyl, a C$_{3~8}$ cycloalkyl, a C$_{3~8}$ heterocyclic group, a C$_{6-20}$ aryl group, a C$_{5-20}$ heteroaryl group, hydroxyl group, mercapto group, carboxyl group, ester group, acyl group, amino group, amide group, sulfonyl group, cyano group, or R$_{3'}$ and R$_{4'}$ together with the connected C and L$_2$ form a 3-10 membered heterocyclic group containing at least one heteroatom or a 5-10 membered heteroaryl group containing at least one heteroatom;

R$_6$ is selected from the following substituted or unsubstituted groups: hydrogen, halogen, a C$_{1~8}$ alkyl, a C$_{1~8}$ alkoxy, a C$_{1~8}$ haloalkyl, a C$_{3~8}$ cycloalkyl, a C$_{3~8}$ heterocyclyl, a C$_{6~20}$ aryl, a C$_{5~20}$ heteroaryl, hydroxyl, mercapto, carboxy, ester, acyl, amino, amido, sulfonyl or cyano;

Z represents C or heteroatom as a ring atom;

n represents an integer from 1 to 10;

the substituents of the above-mentioned groups may be selected from halogen, a C$_{1~8}$ alkyl, a C$_{1~8}$ haloalkyl, a C$_{1~8}$ alkoxy, a C$_{3~8}$ cycloalkyl, a C$_{3~8}$ heterocyclyl, a C$_{6~20}$ aryl, a C$_{5~20}$ heteroaryl, hydroxyl, mercapto, carboxy, ester, acyl, amino, amido, sulfonyl or cyano;

the above-mentioned heteroatoms are selected from N, O or S.

Alternatively, the unsaturated monocyclic ring in formula (1) may also be replaced with other similar structures, for example, adding one or more heteroatoms such as O, S, N and the like to the ring. For examples, the ring atom "Z" shown in formula (1) may represent N.

Alternatively, the binary heteroaryl in formula (1)

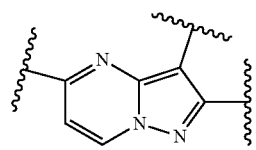 [SMILES: *c1ccn2nc(*)c(*)c2n1]

may also be replaced with other similar structures, such as changing the substitution position of N atoms, adding or removing one or more N atoms in the ring, etc. preferably, it may be replaced with the following structures:

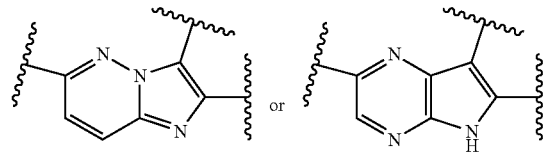

In the Formula (1), the groups represented by R$_a$, R$_b$, R$_1$, R$_2$, R$_3$, R$_4$, R$_{3'}$, R$_{4'}$, R$_5$, R$_6$ and the optional substituents thereof include, but are not limited to:

Hydrogen may be expressed as —H, and may also be replaced with the isotope such as deuterium and tritium.

Halogen may include fluorine, chlorine, bromine, and iodine.

C$_{1~8}$ alkyl may include methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, tert-butyl, n-pentyl, iso pentyl, neopentyl, tert-pentyl, hexyl, heptyl, octyl, etc.

C$_{1~8}$ alkoxy may be represented as —OC$_{1~8}$ alkyl, wherein C$_{1~8}$ alkyl includes those defined as above. For example, C$_{1~8}$ alkoxy group may include methoxy, ethoxy, n-propoxy, isopropoxy, n-butoxy, isobutoxy, sec-butoxy, tert-butoxy, etc.

C$_{1~8}$ haloalkyl may be represented as a group in which any number of hydrogen atoms in C$_{1~8}$ alkyl group is substituted by halogen, wherein C$_{1~8}$ alkyl and halogen are defined as above. For example, C$_{1~8}$ haloalkyl may include —CF$_3$ and the like.

C$_{3~8}$ cycloalkyl may be expressed as a non-aromatic saturated carbocyclic ring, including single-carbon ring (with one ring) and bi-carbon ring (with two rings). For example, C$_{3~8}$ cycloalkyl may include

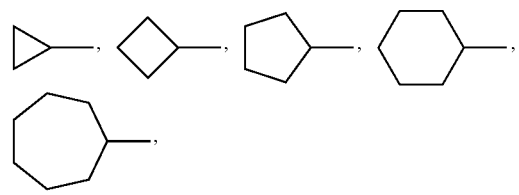

or the like.

C$_{3~8}$ heterocyclic group may be represented as a group obtained by replacing any number of ring atoms in C$_{3~8}$ cycloalkyl with heteroatoms such as O, S, N, P, Si, etc, wherein C$_{3~8}$ cycloalkyl includes those defined as above. For example, C$_{3~8}$ heterocyclic group may include oxiranyl, sulfiethanyl, azaethyl, azetidinyl, oxbutanyl, thibutyryl, tetrahydrofuranyl, pyrrolidinyl, oxazolidinyl, tetrahydropyrazolyl, pyrrolinyl, dihydrofuranyl, dihydrothienyl, piperidinyl, tetrahydropyranyl, tetrahydrothiopyranyl, morpholinyl, piperazinyl, dihydropyridinyl, tetrahydropyranyl, dihydropyranyl, tetrahydropyranyl, dihydrothiopyranyl, azacycloheptyl, oxacycloheptyl, thiacycloheptyl, oxaaza bicyclo[2.2.1]heptyl, azaspiro[3.3]heptyl, etc.

$C_{6-20}$ aryl may include a monocyclic aryl group, a bicyclic aryl group, or a multi-ring aryl group. For example, it may include phenyl, biphenyl, naphthyl, phenanthryl, anthryl, azulenyl, and the like.

$C_{5-20}$ heteroaryl may represent an unsaturated group containing any number of heteroatoms such as O, S, N, P, and Si as ring atoms. For example, $C_{5-20}$ heteroaryl groups may include pyrrolyl, furyl, thienyl, imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, etc.

Hydroxyl may be expressed as —OH.

Mercapto may be represented as —SH.

Carboxyl may be represented as —COOH.

The ester group may be expressed as —COOR', and the definition of R' may be the definition of the substituent described in formula (1). For example, an ester group substituted with a $C_{1-8}$ alkyl group may be expressed as —COOC$_{1-8}$ alkyl, where $C_{1-8}$ alkyl group includes the groups as defined above.

The acyl group may be represented as —COR', and the definition of R' may be the definition of the substituent described in formula (1). For example, an acyl group substituted with a $C_{1-8}$ alkyl group may be represented as —COC$_{1-8}$ alkyl, where $C_{1-8}$ alkyl included the groups as defined above.

The amino group may be represented as —NH$_2$, —NHR' or —N(R')$_2$, and the definition of R' may be the definition of the substituent described in formula (1). For example, an amino group substituted with a $C_{1-8}$ alkyl group may represent —NHC$_{1-8}$ alkyl or —N(C$_{1-8}$ alkyl)$_2$, where C1~8 alkyl includes groups as defined above.

The amide group may be represented as a —CO amino group, where the amino group is defined as above.

The sulfonyl group may be represented as —S(O)$_2$R', and the definition of R' may be the definition of the substituent described in formula (1). For example, a sulfonyl group substituted with a $C_{1-8}$ alkyl group may be represented as —S(O)$_2$C$_{1-8}$ alkyl, wherein $C_{1-8}$ alkyl includes groups as defined above.

The cyano group may be represented as —CN.

In the foregoing definitions, when the number of carbon atoms changes, the above definitions only change according to the change in the number of carbon atoms, and does not affect the definition of the group type. For example, "$C_{1-5}$ alkyl" may include all groups meeting number of carbon atoms of 1 to 5 in the definition of "$C_{1-8}$ alkyl", such as methyl, ethyl, and n-propyl, isopropyl, n-butyl, isobutyl, sec-butyl, tert-butyl, n-pentyl, isopentyl, neopentyl, etc.

Furthermore, in the above formula (1), the groups $R_a$, $R_b$, $R_1$, $R_2$, $R_3$, $R_4$, $R_{3'}$, $R_{4'}$, $R_5$, $R_6$ and their optional substituents include but are not limited to: hydrogen, deuterium, fluorine, chlorine, bromine, methyl, ethyl, propyl, isopropyl, n-butyl, sec-butyl, tert-butyl, methoxy, ethoxy, propoxy, isopropoxy, —CN, —CF$_3$, —NH$_2$, —NH(C$_{1-4}$ alkyl), —N(C$_{1-4}$ alkyl)$_2$, —CO$_2$C$_{1-4}$ alkyl, —CO$_2$H, —NHC(O)C$_{1-4}$ alkyl, —SO$_2$C$_{1-4}$alkyl, —C(O)NH$_2$, —C(O)NH(C$_{1-4}$alkyl), —C(O)N(C$_{1-4}$alkyl)$_2$, cyclopropyl, cyclobutyl, cyclopentyl, cyclohexyl, pyrrolidinyl, pyrazolyl, piperidinyl, pyridyl, piperazinyl, triazinyl, furanyl, thiofuranyl, morpholinyl, thiomorpholinyl, phenyl, naphthyl, diphenyl, terphenyl, etc.

In one embodiment according to the present disclosure, the compound is represented by formula (2),

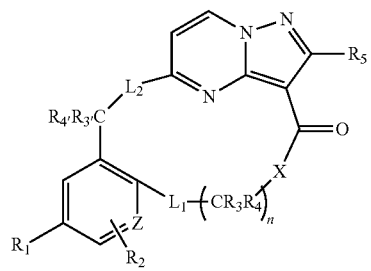

Formula (2)

wherein in formula (2), R1 is selected from fluorine or bromine.

In one embodiment according to the present disclosure, $R_2$ in formula (1) or formula (2) is selected from hydrogen, fluorine or bromine.

In one embodiment according to the present disclosure, $L_1$ in formula (1) or formula (2) is selected from —O—, —S— or a single bond. The single bond in this disclosure means that there is no Li group, that is, the C in the one —(CR$_3$R$_4$)— farthest from the X group is directly connected to the unit aromatic ring.

In one embodiment according to the present disclosure, $L_2$ in formula (1) or formula (2) is selected from —NR$_6$—.

In one embodiment according to the present disclosure, n in formula (1) or formula (2) represents an integer of 2, 3, 4, 5 or 6.

In one embodiment according to the present disclosure, when the substituents R3 and R4 on the C atom in formula (1) or formula (2) together with the group X form a cycloalkyl group, a heterocyclic group or a heteroaryl group, it means that $R_3$ or $R_4$ in the —(CR$_3$R$_4$)— group adjacent to the X group together with the C to which it is connected and X group forms these groups.

In one embodiment according to the present disclosure, in formula (1) or formula (2), when $R_3$ and $R_4$ are each independently a single bond connecting the C atom and adjacent macrocyclic ring atoms, the adjacent macrocyclic ring atom may be a ring atom C in another —(CR$_3$R$_4$)— group adjacent to it, or may be a ring atom in an adjacent X group. In a preferred embodiment, $R_3$ and $R_4$ in the —(CR$_3$R$_4$)— group adjacent to the X group may each independently be a single bond connecting the C atom and the X group, that is, $R_3$ and/or $R_4$ is a single bond connecting the C atom and the X central atom (ie, C in —CR$_a$R$_b$—). For example, when one of $R_3$ and $R_4$ is a single bond, the X group and the adjacent —(CR$_3$R$_4$)— group form a double bond; when both $R_3$ and $R_4$ are single bonds, the X group and the adjacent —(CR$_3$R$_4$)— group form a triple bond.

Similarly, a substituted or unsubstituted double bond or triple bond may also be formed between two adjacent —(CR$_3$R$_4$)— groups in the macrocyclic ring, and between C and C atoms.

In one embodiment according to the present disclosure, in formula (1) or formula (2), the substituents $R_3$ and $R_4$ on each C atom are each independently selected from the following substituted or unsubstituted groups: hydrogen, halogen, a $C_{1-5}$ alkyl, a $C_{1-5}$ alkoxy, a $C_{1-5}$ haloalkyl, a $C_{3-6}$ cycloalkyl or $R_3$ and $R_4$ are each independently a single bond connecting the C atom and adjacent macrocyclic ring atoms.

In an embodiment according to the present disclosure, in formula (1) or formula (2), $R_{3'}$ and $R_{4'}$ are each independently selected from the following substituted or unsubstituted groups: hydrogen, halogen, a $C_{1\sim5}$ alkyl, a $C_{1\sim5}$ alkoxy, a $C_{1\sim5}$ haloalkyl, a $C_{3\sim6}$ cycloalkyl, or $R_{3'}$ and $R_{4'}$ together with the connected C and $L_2$ form a 4- to 8-membered heterocyclic group containing at least one heteroatom. Preferably, the heterocyclic group here may be pyrrolidinyl or piperidinyl, where N is derived from $L_2$.

In an embodiment according to the present disclosure, in formula (1) or formula (2), the macrocyclic atom C in the —$CR_3R_4$— group or the —$CR_3$—$R_4$— group or the C in the substituent group may create one or more chiral centers due to the different groups, and the present disclosure includes all optical isomers and racemates.

In one embodiment according to the present disclosure, in formula (1) or formula (2), $R_5$ is selected from the following substituted or unsubstituted groups: hydrogen, halogen, a $C_{1\sim5}$ alkyl, a $C_{1\sim5}$ alkoxy, a $C_{1\sim5}$ haloalkyl, a $C_{3\sim6}$ cycloalkyl, hydroxyl, mercapto, carboxyl, amino or cyano.

In an embodiment according to the present disclosure, in formula (1) or formula (2), $R_6$ is selected from the following substituted or unsubstituted groups: hydrogen, halogen, a $C_{1\sim5}$ alkyl, a $C_{1\sim5}$ alkoxy, a $C_{1\sim5}$ haloalkyl or a $C_{3\sim6}$ cycloalkyl.

In an embodiment according to the present disclosure, the optional substituents in the above embodiments are selected from fluorine, bromine, —CN, —OH, —$CF_3$, —$NH_2$, —NH($C_{1\sim4}$ alkyl), —N($C_{1\sim4}$ alkyl)$_2$, —$CO_2C_{1\sim4}$ alkyl, —$CO_2H$, —NHC(O)$C_{1\sim4}$ alkyl, —$SO_2C_{1\sim4}$ alkyl, —C(O)$NH_2$, —C(O)NH($C_{1\sim4}$ alkyl), —C(O)N($C_{1\sim4}$ alkyl)$_2$, a $C_{1\sim5}$ alkyl, a $C_{3\sim6}$ cycloalkyl, a $C_{3\sim6}$ heterocyclyl, a $C_{6\sim10}$ aryl or a $C_{5\sim10}$ heteroaryl.

In one embodiment according to the present disclosure, the compound is selected from the following structures:

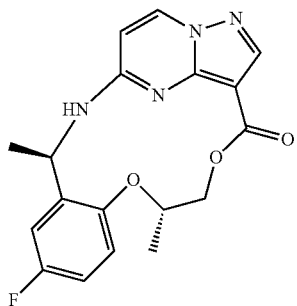

1

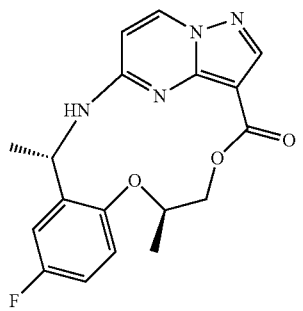

2

-continued

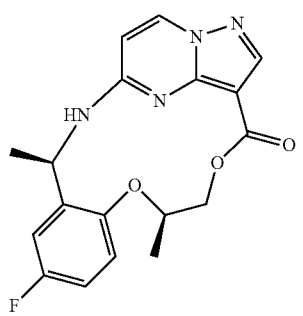

3

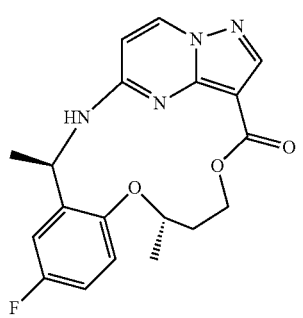

4

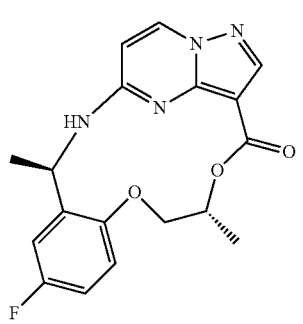

5

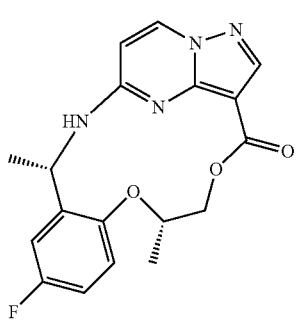

6

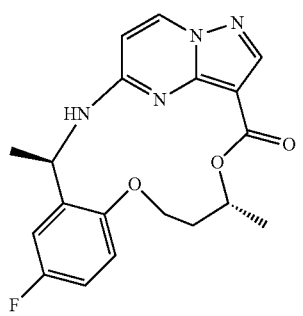

7

8
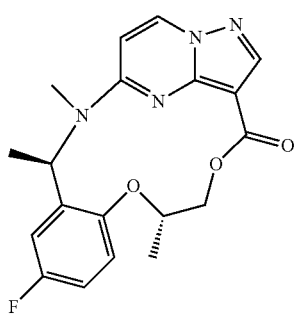
9
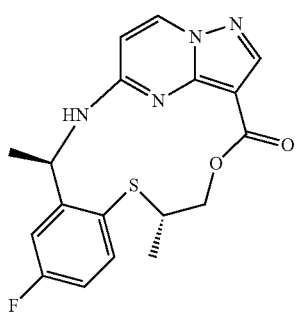
10
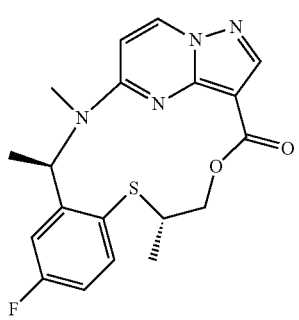
11
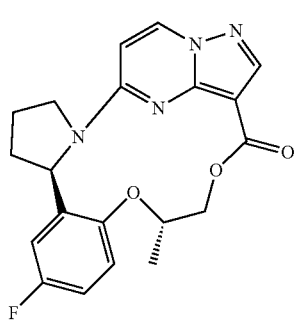
12
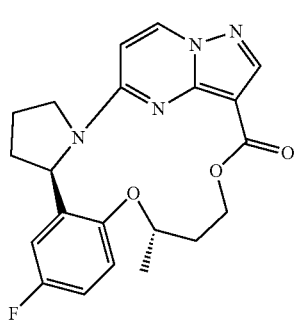
13
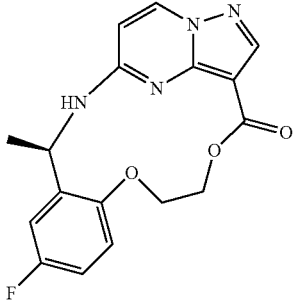
14
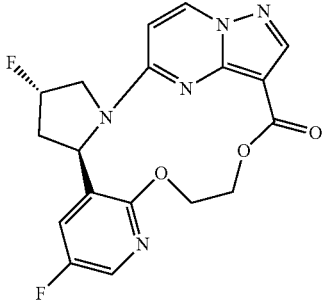
15
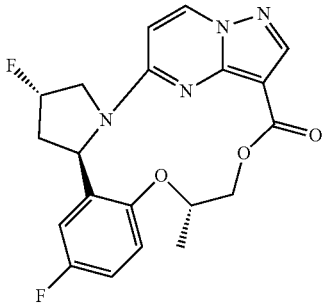
16
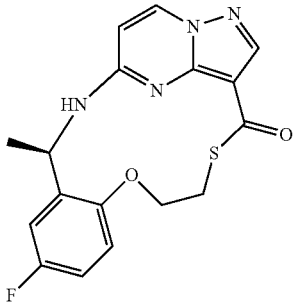
17
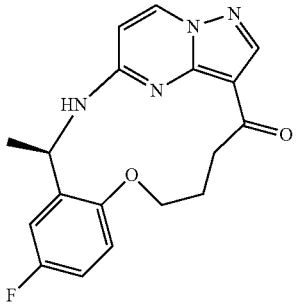

18

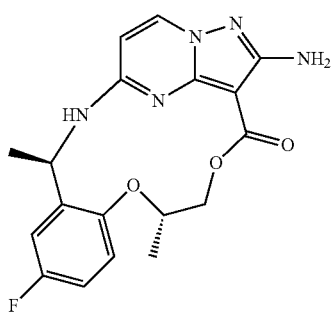

19

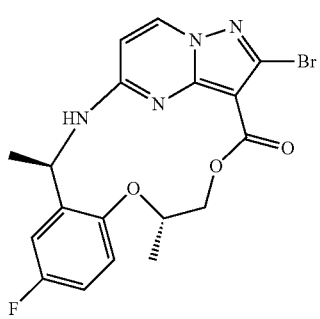

20

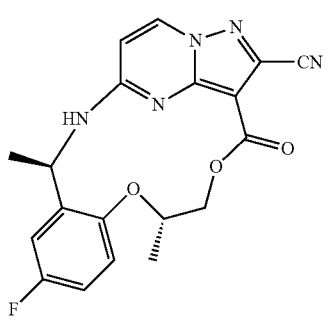

21

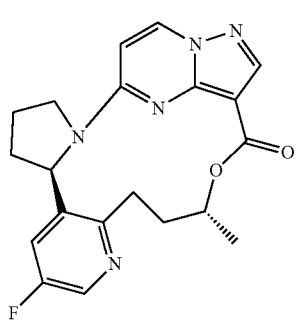

22

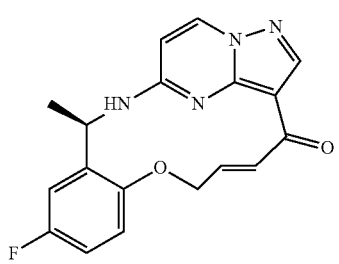

23

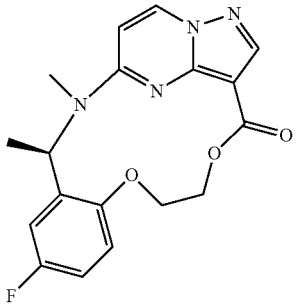

24

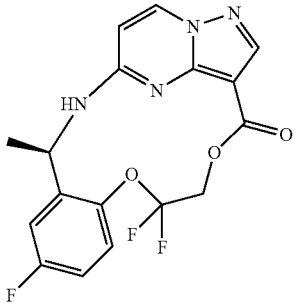

or

25

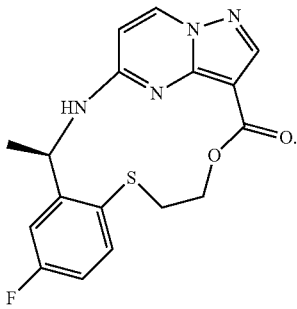

The present disclosure also provides a pharmaceutical composition comprising the compound described in any one of the above technical solutions or a pharmaceutically acceptable salt, a solvate, an active metabolite, a polymorph, an isotope label, an isomer or a prodrug thereof, and a pharmaceutically acceptable carrier.

The pharmaceutical composition includes, but is not limited to, oral dosage form, parenteral dosage form, external dosage form, rectal dosage form and the like. For example, the pharmaceutical composition may be oral tablets, capsules, pills, powders, sustained-release preparations, solutions and suspensions, sterile solutions, suspensions or emulsions for parenteral injection, ointments, creams, gels for external use, etc., or suppositories for rectal administration.

The pharmaceutical composition may also include other active ingredients or drugs, which may be used in combination with the compound or a pharmaceutically acceptable salt, a solvate, an active metabolite, a polymorph, an isotope label, an isomer or a prodrug thereof.

The present disclosure also provides the use of the above mentioned compounds or a pharmaceutically acceptable salt, a solvate, an active metabolite, a polymorph, an isotope label, an isomer or a prodrug thereof, and the above-mentioned pharmaceutical composition in the preparation of a medicament for treating tyrosine kinase-mediated diseases.

Furthermore, the tyrosine kinase is selected from one or more of the following: ALK, ROS1, TRKA, TRKB, TRKC, JAK2, SRC, FYN, LYN, YES, FGR, FAK, AXL, ARK5.

Furthermore, the tyrosine kinase-mediated diseases include cancer, pain, neurological diseases, autoimmune diseases and inflammation.

Furthermore, the tyrosine kinase-mediated cancer may include lung cancer, colorectal cancer, breast cancer, ovarian cancer, thyroid cancer, prostate cancer, hepatocellular carcinoma, renal cell carcinoma, gastric and esophageal cancer, cholangiocarcinoma, glioma, glioblastoma, head and neck cancer, inflammatory myofibroblastic tumor, angiosarcoma, epithelioid hemangioendothelioma, anaplastic large cell lymphoma, etc.

Furthermore, the pain mediated by the tyrosine kinase may be pain of any source or cause, including cancer pain, chemotherapy pain, nerve pain, injury pain or other sources.

Furthermore, the autoimmune diseases mediated by tyrosine kinases include rheumatoid arthritis, Sjogren syndrome, type I diabetes, lupus and the like.

Furthermore, the neurological diseases mediated by the tyrosine kinase include Alzheimer's Disease, Parkinson's Disease, Amyotrophic Lateral Sclerosis, Huntington's Disease (Huntington's disease), or the like.

Furthermore, the tyrosine kinase-mediated inflammatory diseases include atherosclerosis, allergies, inflammation caused by infection or injury, and the like.

The diaryl macrocyclic compound and the pharmaceutical composition provided by the present disclosure have significant activity for inhibiting tyrosine kinase, may overcome tumor drug resistance, and break through the blood-brain barrier, and also have excellent pharmacokinetic properties and excellent oral administration bioavailability. It may be administered in a small dosage, thereby reducing treatment cost and possible side effects to a patient. Thus, the application potential is very great.

Definitions

Unless otherwise defined, all scientific and technological terms herein have the same meanings as commonly understood by those skilled in the art to which the subject of the claims belongs. Unless otherwise specified, all patents, patent applications, and publications cited in this disclosure are incorporated herein by reference in their entirety. When a trade name appears in this disclosure, it refers to its corresponding commodity or its active ingredient.

It should be understood that the foregoing summary and the following detailed description are exemplary and only for explanation, and do not impose any limitation on the subject of the present disclosure. In this application, it must be noted that unless the context clearly indicates otherwise, the singular form used in this specification and claims includes the plural form of the thing referred to. It should also be noted that the use of "or" and "or" means "and/or" unless stated otherwise. In addition, the term "comprise" and other forms such as "comprising", "containing" and "including" are not limiting.

Definitions of standard chemical terms may be found in the literature, including Carey and Sundberg's "Advanced Organic Chemistry 4$^{th}$ Ed, Vol A (2000) and B (2001), Plenum Press, New York. Unless otherwise specified, conventional methods within the technical field are applied, such as mass spectrometry, NMR, HPLC, protein chemistry, biochemistry, recombinant DNA technology, and pharmacological methods. Unless specific definitions are provided, those skilled in the art know the related terms and laboratory operations and techniques in analytical chemistry, synthetic organic chemistry, and medical and pharmaceutical chemistry used in this disclosure. Standard techniques may be used for chemical synthesis, chemical analysis, drug preparation, formulation, drug delivery and patient treatment. Standard techniques may be used for recombinant DNA, oligonucleotide synthesis, and tissue culture and transformation (such as electroporation, lipid infection). For example, a kit with instructions provided by the manufacturer may be used, or the reaction and purification techniques may be carried out according to methods known in the art, or according to the method described in the present disclosure. Generally speaking, the aforementioned techniques and steps may be implemented by conventional methods well-known in the art and described in various general documents or more specific documents. These documents are described and cited in the present disclosure.

When a substituent is described by a conventional chemical formula written from left to right, the substituent also includes chemically equivalent substituents obtained when the structural formula is written from right to left. For example, $CH_2O$ is equivalent to $OCH_2$.

The term "substituted" means that any one or more hydrogen atoms on a specific atom are replaced by a substituent, as long as the valence of the specific atom is normal and the compound after substitution is stable. When the substituent is oxo (ie =O), it means that two hydrogen atoms are replaced, and the oxo will not occur on the aromatic group.

When any variable (such as R) occurs more than once in the composition or structure of a compound, its definition in each case is independent. Thus, for example, if a group is substituted with 0-2 Rs, the group may optionally be substituted with up to two Rs, and R has independent options in each case. In addition, combinations of substituents and/or variants thereof are only permitted if such combinations result in stable compounds.

As used herein, $C_{m-n}$ refers to the part having m-n carbon atoms. For example, the "$C_{1-8}$" group means that the part has 1-8 carbon atoms, that is, the group contains 1 carbon atom, 2 carbon atoms, 3 carbon atoms . . . 8 carbon atoms. Therefore, for example, "$C_{1-8}$ alkyl" refers to an alkyl containing 1-8 carbon atoms, that is, the alkyl group is selected from methyl, ethyl, propyl, isopropyl, n-butyl, isopropyl, n-butyl, sec-butyl, tert-butyl . . . octyl, etc. Numerical ranges in this text, for example "1-8" refers to each integer in the given range. For example, "1-8 carbon atoms" means that the group may have 1 carbon atom, 2 carbon atoms, 3 carbon atoms, 4 carbon atoms, 5 carbon atoms, 6 carbon atoms, 7 carbon atoms, or 8 carbon atoms.

The term "member" refers to the number of skeletal atoms constituting the ring. For example, pyridine is a six-membered ring and pyrrole is a five-membered ring.

The term "pharmaceutically acceptable" refers to those compounds, materials, compositions and/or dosage forms that are within the scope of reliable medical judgment and are suitable for use in contact with human and animal tissues without excessive toxicity, irritation, allergic reactions or other problems or complications of the disease, and are commensurate with a reasonable benefit/risk ratio.

The term "pharmaceutical composition" refers to a biologically active compound optionally mixed with at least one pharmaceutically acceptable chemical component or agent. The pharmaceutically acceptable chemical component or agent is the "carrier", which helps for introducing the compound into cells or tissues. It includes, but is not limited to, stabilizers, diluents, suspending agents, thickeners, and/or excipients.

The term "pharmaceutically acceptable salt" refers to a salt that retains the biological efficacy of the free acid and free base of the specified compound and has no adverse effects in biology or other aspects. Unless otherwise specified, the salts in the present disclosure may include metal salts, ammonium salts, salts formed with organic bases, salts formed with inorganic acids, salts formed with organic acids, salts formed with basic or acidic amino acids, etc. Non-limiting examples of metal salts include, but are not limited to, alkali metal salts, such as sodium salt, potassium salt, etc.; alkaline earth metal salts, such as calcium salt, magnesium salt, barium salt, etc.; aluminum salt, and the like. Non-limiting examples of salts formed with organic bases include, but are not limited to, the salts formed with trimethylamine, triethylamine, pyridine, picoline, 2,6-lutidine, ethanolamine, diethanolamine, triethanolamine, cyclohexylamine, dicyclohexylamine and the like. Non-limiting examples of salts formed with inorganic acids include, but are not limited to, salts formed with hydrochloric acid, hydrobromic acid, nitric acid, sulfuric acid, phosphoric acid, and the like. Non-limiting examples of salts formed with organic acids include, but are not limited to, salts formed with formic acid, acetic acid, trifluoroacetic acid, fumaric acid, oxalic acid, malic acid, maleic acid, tartaric acid, citric acid, succinic acid, methanesulfonic acid, benzene sulfonic acid, p-toluenesulfonic acid, etc. Non-limiting examples of salts formed with basic amino acids include, but are not limited to, salts formed with arginine, lysine, ornithine, and the like. Non-limiting examples of salts formed with acidic amino acids include, but are not limited to, salts formed with aspartic acid, glutamic acid, and the like.

Pharmaceutically acceptable salts may be synthesized from parent compounds containing acid radicals or bases by conventional chemical methods. Generally, such salts are prepared by reacting these compounds in free acid or base form with a stoichiometric amount of appropriate base or acid in water or organic solvent or a mixture of both. Generally, non-aqueous media such as ether, ethyl acetate, ethanol, isopropanol or acetonitrile are preferred.

The term "solvate" refers to a physical aggregate formed by a compound of the present disclosure and one or more solvent molecules. This physical aggregate includes varying degrees of ions and covalent bonds, such as hydrogen bonds. It has been shown that this solvate may be separated, for example, when one or more solvent molecules are mixed in the crystal lattice. "solvate" includes both solvent phase and separable solvate. There are many examples of corresponding solvates, including ethanol solvates, methanol solvates and the like. "Hydrate" is a solvate that uses water ($H_2O$) molecules as a solvent. One or more compounds in the present disclosure may be prepared as solvates at will. The preparation of solvates is well known. For example, M. Caira et al, J. Pharmaceutical Sci., 93(3), 601-611 (2004) describe the preparation of a solvate of the antifungal drug fluconazole, that is, preparation with ethyl acetate and water. E. C. van Tonder et al, AAPS Pharm Sci Tech., 5(1), article 12 (2004); and A L Bingham et al, Chem. Commun., 603-604 (2001) also describes the similar methods for preparing solvates and hydrates. A typical, non-limiting preparation process is to dissolve the compound of the present disclosure in an ideal solvent (organic solvent or water or their mixed solvent) at a temperature higher than normal temperature, to cool down, and to leave to crystallize. Then the crystals are separated by use standard methods. The I. R. spectroscopy analysis technique may confirm the existence of the solvent (water) that forms the solvate (hydrate) in the crystal.

The term "active metabolite" refers to an active derivative of the compound formed when the compound is metabolized.

The term "polymorphs" refers to compounds of the present disclosure that exist in different crystal lattice forms.

The term "isotopic label" refers to an isotopically labeled compound of the present disclosure. For example, the isotopes in the compound of the present disclosure may include various isotopes of elements such as H, C, N, O, P, F, S, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}S$.

The term "pharmaceutically acceptable prodrug" or "prodrug" refers to any pharmaceutically acceptable salt, ester, ester salt or other derivative of the compound of the present disclosure, which may directly or indirectly provide the compound of the present disclosure or its pharmaceutically active metabolite or residue after administration to a recipient. Particularly preferred derivatives or prodrugs are those compounds that may improve the bioavailability of the compounds of the present application when administered to patients (for example, may make oral compounds more easily absorbed into the blood), or promote the parent compound delivering to biological organs or the site of action, such as the brain or lymphatic system. The functional groups in the compound may be modified by conventional operations or in vivo in a modification manner that may be decomposed into the parent compound to prepare a prodrug. Various prodrug forms are well known in the art. See, Pro-drugs as Novel Delivery Systems (1987) Vol. 14 of the ACS Symposium Series, Bioreversible Carriers in Drug Design, (1987) Edward B. Roche, ed., American Pharmaceutical Association by T. Higuchi and V. Stella and Pergamon Press provide discussions on prodrugs. Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, pp. 113-191; and Bundgaard, H., Advanced Drug Delivery Review, 1992, 8, 1-38, the above documents are incorporated herein by reference.

The term "stereoisomers" refers to isomers produced by different arrangements of atoms in the molecule in space. The compounds of the present disclosure contain structures such as asymmetric or chiral centers and double bonds. Therefore, the compounds of the present disclosure may include optical isomers, geometric isomers, tautomers, atropisomers and other isomers. These isomers and their single isomers, racemates, etc. are all included in the scope of the present disclosure. For example, for optical isomers, optically active (R)- and (S)-isomers and D and L isomers may be prepared by chiral resolution, chiral synthesis or chiral reagents or other conventional techniques. For example, it may be converted into diastereomers by reacting with appropriate optically active substances (such as chiral alcohols or Mosher's Mohsyl chloride), separated and converted (such as hydrolyzed) into the corresponding single isomer. For another example, it may also be separated by a chromatographic column.

The "pharmaceutical compositions" herein may be prepared in a manner well known in the pharmaceutical field, and they may be administered or applied by various routes, depending on whether local or systemic treatment is required and the area to be treated. It may be topically administered (for example, transdermal, skin, eye and mucous membranes including intranasal, vaginal and rectal delivery), pulmonarily administered (for example, by inhalation or insufflation of powder or aerosol, including through sprayers; intratracheal, intranasal), orally or parenterally administered. Parenteral administration includes intravenous, intraarterial, subcutaneous, intraperitoneal or intramuscular injection or infusion; or intracranial, such as intrathecal or intracerebroventricular administration. It may be administered parenterally in a single bolus dose, or it may be administered by, for example, a continuous infusion pump. The pharmaceutical composition herein includes but is not limited to the following forms: tablets, pills, powders, lozenges, sachets, cachets, elixirs, suspensions, emulsions, solutions, syrups, aerosols (solid or dissolved in a liquid vehicle); for example, ointments, soft and hard gelatin capsules, suppositories, sterile injection solutions and sterile packaged powders containing up to 10% by weight of the active compound.

The pharmaceutical composition herein may be formulated in a unit dosage form, and each dosage may contain about 0.1 to 1000 mg, usually about 5 to 1000 mg of active ingredient, and more usually about 100 to 500 mg of active ingredient. The term "unit dosage form" refers to a physically separated single dosage unit suitable for use in human patients and other mammals, each unit containing a predetermined amount of active substance mixed with a suitable pharmaceutical carrier calculated to produce the desired therapeutic effect.

The term "individual" refers to an individual suffering from a disease, disorder, or condition, and includes mammals and non-mammals. Examples of mammals include, but are not limited to, any member of the class Mammals: humans, non-human primates (such as chimpanzees and other apes and monkeys); domestic animals, such as cows, horses, sheep, goats, and pigs; domesticated animals, such as rabbits, dogs, and cats; laboratory animals, including rodents, such as rats, mice, and guinea pigs.

The term "treatment" and other similar synonyms include alleviation, reduction or amelioration of symptoms of a disease or condition, prevention of other symptoms, amelioration or prevention of the underlying metabolic cause of the symptoms, inhibition of the disease or condition, such as preventing the development of the disease or condition, alleviating the disease or condition, making a disease or condition better, alleviating the symptoms caused by the disease or condition, or stopping the symptoms of the disease or condition. In addition, the term may also include the purpose of prevention. The term also includes obtaining therapeutic effects and/or preventive effects. The therapeutic effect refers to curing or improving the underlying disease being treated. In addition, the cure or improvement of one or more physiological symptoms associated with the underlying disease is also a therapeutic effect. For example, although the patient may still be affected by the underlying disease, an improvement in the patient's condition is observed. In terms of preventive effects, the composition or compound may be administered to patients who are at risk of suffering from a specific disease, or even if a disease diagnosis has not been made, the composition or compound may be administered to patients who have one or more physiological symptoms of the disease.

The term "amount to obtain the necessary therapeutic effect" or "therapeutically effective amount" refers to the amount of at least one agent or compound sufficient to relieve one or more symptoms of the disease or condition being treated after administration. The result may be a reduction and/or alleviation of signs, symptoms or causes, or any other desired changes in the biological system. Techniques such as dose escalation tests may be used to determine the effective amount suitable for any individual case. The actual amount of compound, pharmaceutical composition or agent to be administered is usually determined by the physician according to the relevant circumstances, including the condition being treated, the route of administration selected, the actual compound administered; the age, weight and response of the individual patient; and the severity of the patient's symptoms, etc.

The ratio or concentration of the compound of the present disclosure in the pharmaceutical composition may not be fixed, depending on various factors, including dosage, chemical properties (for example, hydrophobicity), route of administration, and the like. For example, the compound of the present disclosure may be provided by a physiologically buffered aqueous solution containing about 0.1-10% w/v of the compound for parenteral administration. Some typical dosage ranges are from about 1 μg/kg to about 1 g/kg body weight/day. In certain embodiments, the dosage range is from about 0.01 mg/kg to about 100 mg/kg body weight/day. The dosage is likely to depend on such variables, such as the type and degree of development of the disease or condition, the general health status of the specific patient, the relative biological efficacy of the selected compound, the excipient formulation and its route of administration.

The term "administration" refers to a method capable of delivering a compound or composition to a desired site for biological action. These methods include, but are not limited to, oral routes, transduodenal routes, parenteral injections (including intravenous, subcutaneous, intraperitoneal, intramuscular, intraarterial injection or infusion), topical, and rectal administration. Those skilled in the art are familiar with administration techniques that may be used for the compounds and methods described herein, for example, those discussed in Goodman and Gilman, The Pharmacological Basis of Therapeutics, currented.; Pergamon; and Remington's, Pharmaceutical Sciences (current edition), Mack Publishing Co., Easton, Pa.

The term "$IC_{50}$" refers to 50% inhibition of the maximum effect obtained in an analysis measuring such an effect.

DESCRIPTION OF THE DRAWINGS

FIG. 1 is a schematic diagram of the synthetic route of Example 1.

DETAILED DESCRIPTION

To make the objectives, technical solutions, and advantages of the present disclosure clearer, the technical solutions of the exemplary embodiments of the present disclosure will be further described below.

In the present disclosure, the compounds described in the present disclosure may be prepared by the following methods. The following methods and examples are to illustrate these methods. These procedures and examples should not be construed as limiting the present disclosure in any way. The compounds described herein may also be synthesized using standard synthesis techniques known to those skilled in the art, or methods known in the art and methods described herein may be used in combination.

In the present disclosure, the compounds described in the present disclosure may be prepared by the following methods. The following methods and examples are to illustrate these methods. These procedures and examples should not be construed as limiting the present disclosure in any way.

The compounds described herein may also be synthesized using standard synthesis techniques known to those skilled in the art, or methods known in the art and methods described herein may be used in combination.

The chemical reactions in the embodiments of the present disclosure are completed in a suitable solvent, and the solvent must be suitable for the chemical changes of the present disclosure and the reagents and materials required. In order to obtain the compounds of the present disclosure, it is sometimes necessary for those skilled in the art to modify or select the synthesis steps or reaction schemes based on the existing embodiments.

An important consideration in the planning of any synthetic route in the art is to select an appropriate protecting group for the reactive functional group (such as the amino group in the present disclosure). For trained practitioners, Greene and Wuts (Protective Groups In Organic Synthesis, Wiley and Sons, 1991) is the authority in this regard. All references cited in the present disclosure are incorporated into the present disclosure in their entirety.

The reactions described herein may be monitored according to any suitable method known in the art. For example, product formation may be monitored by a broad spectrum method such as nuclear magnetic resonance spectroscopy (such as $^1H$ or $^{13}C$), infrared spectroscopy, spectrophotometry (such as UV-visible light), mass spectrometry, etc., or chromatography such as high performance liquid chromatography (HPLC) or thin layer chromatography.

Example 1: ($1^3E,1^4E,3R,6S$)-$4^5$-fluoro-3,6-dimethyl-5,8-dioxa-2-aza-1(5,3)-pyrazolo[1,5-a]pyrimidina-4(1,2)-benzenacyclononaphan-9-one

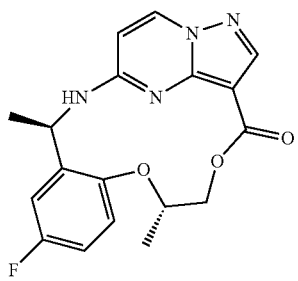 [SMILES: C[C@H]1COC(=O)c2cnn3ccc(nc23)N[C@H](C)c2cc(F)ccc2O1]

Synthetic route was shown in FIG. 1.

Step A: (E)-N-(5-fluoro-2-hydroxybenzylidene)-2-methylpropane-2-sulfinamide

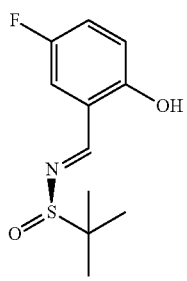 [SMILES: CC(C)(C)[S@@](=O)/N=C/c1cc(F)ccc1O]

5.8 g (41.4 mmol, 1.0 eq) 5-fluoro-2-hydroxybenzaldehyde and 5.0 g (41.4 mmol, 1 eq) (R)-2-methylpropane-2-sulfinamide was added to 100 mL methylene chloride (DCM), then 21.5 g (66.3 mmol, 1.6 eq) $Cs_2CO_3$ was added under magnetic stirring. The resultant solution was stirred at rt for overnight. The mixture was filtered, and the filter cake was rinsed with dichloromethane. The filtrate was concentrated to give the crude product, which was used in next step without further purification (8.5 g, 85% yield).

Step B: N—((R)-1-(5-fluoro-2-hydroxyphenyl)ethyl)-2-methylpropane-2-sulfinamide

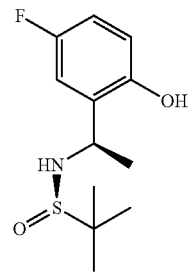 [SMILES: C[C@@H](N[S@](=O)C(C)(C)C)c1cc(F)ccc1O]

24 g (100 mmol, 1.0 eq) (E)-N-(5-fluoro-2-hydroxybenzylidene)-2-methylpropane-2-sulfinamide was added to 300 mL THF and the mixture was cooled to −65° C., 100 mL (3N, 3.0 eq) methyl magnesium bromide was slowly added under $N_2$, and the temperature was maintained below −50° C. After adding, the mixture was slowly rised to room temperature for overnight. TLC analysis ($CH_2Cl_2$: hexane=3:1) showed that the reaction was complete. The reaction mixture was quenched with water (500 mL). 500 mL ethyl acetate (EA) was added for extraction. The combined organic layers were washed twice with water and saturated brine in turn, and dried over anhydrous $Na_2SO_4$. The solvent was removed by concentration to afford the crude product, which was purified by silica gel column chromatography (8.5 g, 33% yield).

$^1H$ NMR (400 MHz, $CDCl_3$) δ 9.02 (s, 1H), 6.79 (d, J=4.0 Hz, 1H), 6.65-6.51 (m, 1H), 6.50-6.41 (m, 1H), 5.04 (d, J=8.0 Hz, 1H), 4.45-4.30 (m, 1H), 1.53 (d, J=8.0 Hz, 3H), 1.29 (s, 9H).

Step C: (R)-2-(1-aminoethyl)-4-fluorophenol hydrochloride

8.5 g (32.8 mmol, 1.0 eq) N—((R)-1-(5-fluoro-2-hydroxyphenyl)ethyl)-2-methylpropane-2-sulfinamide was dissolved in 100 mL dioxane (4N) solution. The reaction was carried out at room temperature for 3 hours, and TLC analysis showed that the reaction was complete. The solvent was removed by concentration. The crude product was dissolved in 100 mL EA, filtered and rinsed with EA. The solid was collected and dried to obtain the target product (5.4 g, 87% yield).

Step D: ethyl (R)-5-((1-(5-fluoro-2-hydroxyphenyl)ethyl)amino)pyrazolo[1,5-a] pyrimidine-3-carboxylate

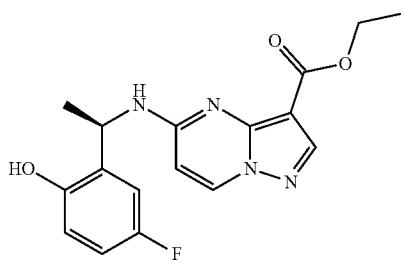 [SMILES: CCOC(=O)c1cnn2ccc(N[C@H](C)c3cc(F)ccc3O)nc12]

5.3 g (27.9 mmol, 1.0 eq) (R)-2-(1-aminoethyl)-4-fluorophenol hydrochloride, 6.29 g (27.9 mmol, 1.0 eq) ethyl 5-chloropyrazolo[1,5-a]pyrimidine-3-carboxylate and diisopropylethylamine (DIEA) (12 mL, 167 mmol, 6.0 eq) were dissolved in 60 ml N,N-dimethylformamide (DMF). The mixture was heated to 120° C. for 5 hours. TLC analysis showed that the reaction was complete, and the solvent was removed by concentration. Water (100 mL) and ethyl acetate (200 mL) were added for extraction. The combined organic layers were washed twice with water and saturated brine in turn, and dried over anhydrous $Na_2SO_4$. The solvent was removed by concentration to afford the crude product, which was purified by silica gel column chromatography (2.9 g, 31% yield).

$^1$H NMR (400 MHz, $CDCl_3$) δ 9.17 (brs, 1H), 8.24 (s, 1H), 8.14 (d, J=8.0 Hz, 1H), 6.93-6.90 (m, 2H), 6.83 (d, J=8.0 Hz, 1H), 6.13 (d, J=8.0 Hz, 1H), 5.81 (d, J=8.0 Hz, 1H), 5.64 (t, J=8.0 Hz, 1H), 4.42 (q, J=8.0 Hz, 2H), 1.61 (d, J=8.0 Hz, 3H), 1.41 (t, 3H).

Step E: (R)-2-hydroxypropyl Pivalate

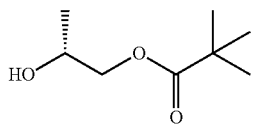

To a solution of (R)-propane-1,2-diol (7.6 g, 100 mmol, 1.0 eq), and pyridine (16 mL, 200 mmol, 2.0 eq) in 80 mL dichloromethane (DCM) was slowly added pivaloyl chloride (12.6 g, 100 mmol, 1.0 eq) at ice bath. After adding, the mixture was rised to room temperature for overnight. TLC analysis showed that the reaction was complete, and the solvent was removed by concentration. Water (100 mL) and ethyl acetate (250 mL) were added for extraction. The combined organic layers were washed twice with water and saturated brine in turn, and dried over anhydrous $Na_2SO_4$. The solvent was removed by concentration to afford the crude product, which was purified by silica gel column chromatography (10.5 g, 66% yield).

Step F: Compound 11

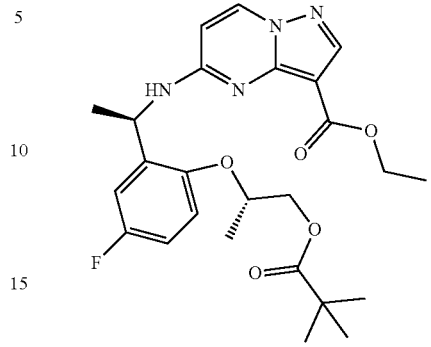

To a solution of (R)-ethyl (R)-5-((1-(5-fluoro-2-hydroxyphenyl)ethyl)amino)pyrazolo[1,5-a]pyrimidine-3-carboxylate (2.0 g, 5.8 mmol, 1.0 eq), (R)-2-hydroxypropyl pivalate (1.39 g, 8.7 mmol, 1.5 eq) and $PPh_3$ (3.04 g, 11.6 mmol, 2.0 eq) in DCM (35 mL) was slowly added diisopropyl azodicarboxylate (DIAD) (2.02 g, 11.6 mmol, 2.0 eq) at ice bath. After adding, the mixture was rised to room temperature for overnight. TLC analysis showed that the reaction was complete, and the solvent was removed by concentration. Water (100 mL) and ethyl acetate (250 mL) were added for extraction. The combined organic layers were washed twice with water and saturated brine in turn, and dried over anhydrous $Na_2SO_4$. The solvent was removed by concentration to afford the crude product, which was purified by silica gel column chromatography (2.1 g, 75% yield).

$^1$H NMR (400 MHz, $CDCl_3$) δ 8.25 (s, 1H), 8.16 (d, J=8.0 Hz, 1H), 7.10 (d, J=8.0 Hz, 1H), 6.90 (d, J=8.0 Hz, 2H), 6.08 (d, J=8.0 Hz, 1H), 5.24 (s, 1H), 4.74-4.65 (m, 1H), 4.38 (q, J=8.0 Hz, 2H), 4.28-4.13 (m, 3H), 1.56 (d, J=8.0 Hz, 3H), 1.40 (t, J=8.0 Hz, 3H), 1.25 (d, J=8.0 Hz, 3H), 1.20 (t, 9H).

Step G: Compound 12

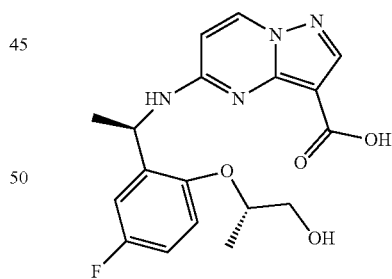

To a solution of compound 11 (1.5 g, 3.1 mmol, 1.0 eq) in MeOH (10 mL) was added NaOH solution (3.1 mL, 10N, 10.0 eq) at ice bath. After adding, the mixture was heated to room temperature for 2.0 hours. TLC analysis showed that the reaction was complete, and the solution was removed by concentration. 1N HCl solution was added until pH 7. The resulting suspension was collected by filtration and washed with 200 mL water. The crude product was dried to obtain the target compound 12 (0.72 g, 63% yield).

$^1$H NMR (400 MHz, DMSO) δ 11.50 (brs, 1H), 8.55 (d, J=9.2 Hz, 1H), 8.28 (d, J=9.2 Hz, 1H), 8.10 (s, 1H), 7.15-6.94 (m, 3H), 6.45 (d, J=9.2 Hz, 1H), 5.61 (d, J=8.0 Hz, 1H), 4.52-4.35 (m, 1H), 3.68-3.42 (m, 2H), 1.43 (d, J=8.0 Hz, 3H), 1.24 (d, J=8.0 Hz, 3H).

Step H: (1³E,1⁴E,3R,6S)-4⁵-fluoro-3,6-dimethyl-5,8-dioxa-2-aza-1(5,3)-pyrazolo[1,5-a]pyrimidina-4(1,2)-benzenacyclononaphan-9-one

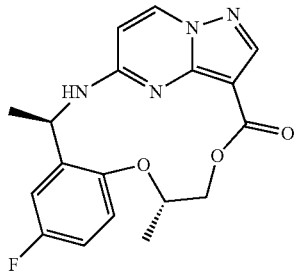 [SMILES: C[C@H]1COC(=O)c2cnn3ccc(nc23)N[C@H](C)c2cc(F)ccc2O1]

To a solution of compound 12 (150 mg, 0.40 mmol, 1.0 eq), 2,4,6-trichlorobenzoyl chloride (489 mg, 2.0 mmol, 5.0 eq) in 10 mL THF was added Et₃N (280 mg, 2.4 mmol, 6.0 eq), the reaction solution was stirred at ambient temperature for 30 min. Then the reaction solution was slowly added to a solution of 4-dimethylaminopyridine (488 mg, 4.0 mmol, 10.0 eq) in 500 mL toluene. The resultant mixture was heated to 100° C. under stirring for 2 hours, then the reaction was stirred at ambient temperature for overnight. TLC analysis showed that the reaction was complete, and the solvent was removed by concentration, and water (30 mL) and EA (50 mL) was added for extraction. The organic layers were washed twice with water and saturated brine. The combined organic layers were dried over anhydrous Na₂SO₄. The solvent was removed by concentration to afford the crude product, which was purified by silica gel column chromatography (23 mg, 16% yield).

LC-MS: m/z=357 [M+H]⁺.

¹H NMR (400 MHz, CDCl₃) δ 8.26-8.20 (m, 2H), 7.01 (d, J=8.0 Hz, 1H), 6.87-6.69 (m, 2H), 6.19 (d, J=4.0 Hz, 1H), 6.01-5.85 (m, 1H), 5.55 (s, 1H), 4.89 (dd, J=8.0, 4.0 Hz, 1H), 4.62 (s, 1H), 4.13 (t, J=8.0 Hz, 1H), 1.63-1.52 (m, 6H).

Example 2: (1³E,1⁴E,3S,6S)-4⁵-fluoro-3,6-dimethyl-5,8-dioxa-2-aza-1(5,3)-pyrazolo[1,5-a]pyrimidina-4(1,2)-benzenacyclononaphan-9-one

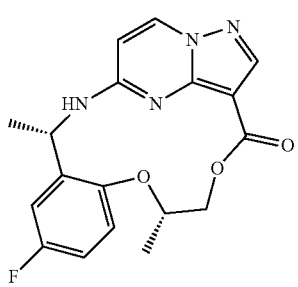 [SMILES: C[C@@H]1Nc2ccn3ncc(c3n2)C(=O)OC[C@H](C)Oc2ccc(F)cc21]

The compound (20 mg, 15%) was prepared according to the steps described in example 1. LC-MS: m/z=357 [M+H]⁺.

Example 3: (1³E,1⁴E,3S,6R)-4⁵-fluoro-3,6-dimethyl-5,8-dioxa-2-aza-1(5,3)-pyrazolo[1,5-a]pyrimidina-4(1,2)-benzenacyclononaphan-9-one

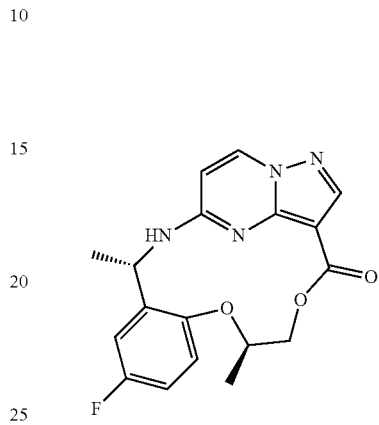

The compound (31 mg, 22%) was prepared according to the steps described in example 1. LC-MS: m/z=357 [M+H]⁺.

Example 4: (1³E,1⁴E,3R,6R)-4⁵-fluoro-3,6-dimethyl-5,8-dioxa-2-aza-1(5,3)-pyrazolo[1,5-a]pyrimidina-4(1,2)-benzenacyclononaphan-9-one

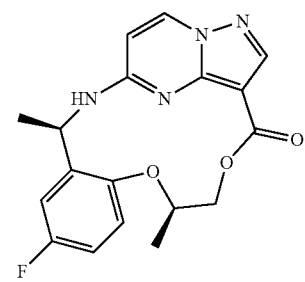 [SMILES: C[C@@H]1COC(=O)c2cnn3ccc(nc23)N[C@H](C)c2cc(F)ccc2O1]

The compound (35 mg, 24%) was prepared according to the steps described in example 1. LC-MS: m/z=357 [M+H]⁺.

The following compounds were prepared by a similar method according to example 1:

Example 5:
($1^3$E,$1^4$E,3R,6S)-$4^5$-fluoro-3,6-dimethyl-5,9-dioxa-2-aza-1(5,3)-pyrazolo[1,5-a]pyrimidina-4(1,2)-benzenacyclodecaphan-10-one

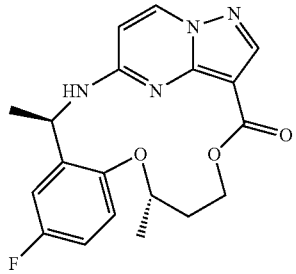 [SMILES: C[C@H]1CCOC(=O)c2cnn3ccc(nc23)N[C@H](C)c2cc(F)ccc2O1]

Example 7:
($1^3$E,$1^4$E,3R,8R)-$4^5$-fluoro-3,8-dimethyl-5,9-dioxa-2-aza-1(5,3)-pyrazolo[1,5-a]pyrimidina-4(1,2)-benzenacyclodecaphan-10-one

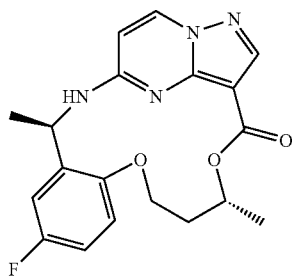 [SMILES: C[C@@H]1CCOc2ccc(F)cc2[C@@H](C)Nc2ccn3ncc(c3n2)C(=O)O1]

Example 8:
($1^3$E,$1^4$E,3R,6S)-$4^5$-fluoro-2,3,6-trimethyl-5,8-dioxa-2-aza-1(5,3)-pyrazolo[1,5-a]pyrimidina-4(1,2)-benzenacyclononaphan-9-one

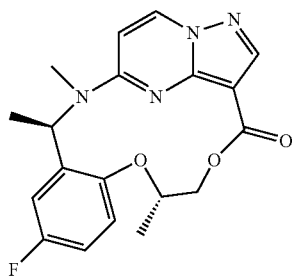 [SMILES: C[C@@H]1c2cc(F)ccc2O[C@@H](C)COC(=O)c2cnn3ccc(nc23)N1C]

Example 10:
($1^3$E,$1^4$E,3R,6S)-$4^5$-fluoro-2,3,6-trimethyl-8-oxa-5-thia-2-aza-1(5,3)-pyrazolo[1,5-a]pyrimidina-4(1,2)-benzenacyclononaphan-9-one

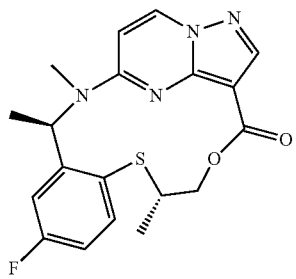 [SMILES: C[C@@H]1c2cc(F)ccc2S[C@@H](C)COC(=O)c2cnn3ccc(nc23)N1C]

Example 11:
($1^3$E,$1^4$E,$2^2$R,5S)-$3^5$-fluoro-5-methyl-4,7-dioxa-1(5,3)-pyrazolo[1,5-a]pyrimidina-2(1,2)-pyrrolidina-3(1,2)-benzenacyclooctaphan-8-one

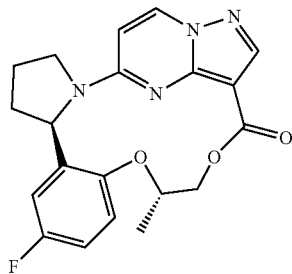 [SMILES: C[C@H]1COC(=O)c2cnn3ccc(nc23)N2CCC[C@@H]2c2cc(F)ccc2O1]

Example 12:
(1³E,1⁴E,2²R,5S)-3⁵-fluoro-5-methyl-4,8-dioxa-1(5,3)-pyrazolo[1,5-a]pyrimidina-2(1,2)-pyrrolidina-3(1,2)-benzenacyclononaphan-9-one

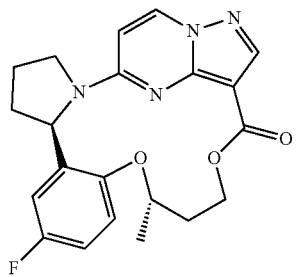 [SMILES: C[C@H]1CCOC(=O)c2cnn3ccc(nc23)N2CCC[C@@H]2c2cc(F)ccc2O1]

Example 14:
(1³E,1⁴E,2²R,5S)-3⁵-fluoro-5-methyl-4,8-dioxa-1(5,3)-pyrazolo[1,5-a]pyrimidina-2(1,2)-pyrrolidina-3(1,2)-benzenacyclononaphan-9-one

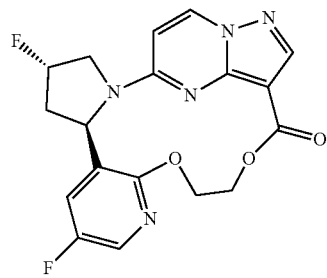 [SMILES: O=C1OCCOc2ncc(F)cc2[C@H]2C[C@H](F)CN2c2ccn3ncc1c3n2]

Example 15:
(1³E,1⁴E,2²R,2⁴S,5S)-2⁴,3⁵-difluoro-5-methyl-4,7-dioxa-1(5,3)-pyrazolo[1,5-a]pyrimidina-2(1,2)-pyrrolidina-3(1,2)-benzenacyclooctaphan-8-one

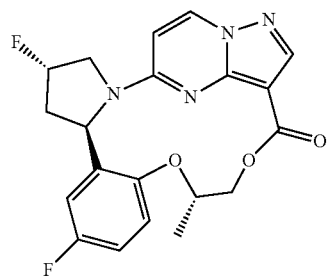 [SMILES: C[C@H]1COC(=O)c2cnn3ccc(nc23)N2C[C@@H](F)C[C@@H]2c2cc(F)ccc2O1]

Example 16:
(R,1³E,1⁴E)-4⁵-fluoro-3-methyl-5-oxa-8-thia-2-aza-1(5,3)-pyrazolo[1,5-a]pyrimidina-4(1,2)-benzenacyclononaphan-9-one

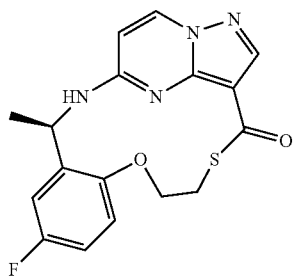 [SMILES: C[C@H]1Nc2ccn3ncc(c3n2)C(=O)SCCOc2ccc(F)cc21]

Example 17:
(R,1³E,1⁴E)-4⁵-fluoro-3-methyl-5-oxa-2-aza-1(5,3)-pyrazolo[1,5-a]pyrimidina-4(1,2)-benzenacyclononaphan-9-one

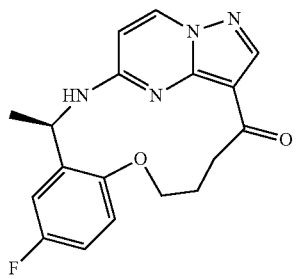 [SMILES: C[C@H]1Nc2ccn3ncc(c3n2)C(=O)CCCOc2ccc(F)cc21]

-continued

Example 18:
(1³E,1⁴E,3R,6S)-1²-amino-4⁵-fluoro-3,6-dimethyl-5,8-dioxa-2-aza-1(5,3)-pyrazolo[1,5-a]pyrimidina-4(1,2)-benzenacyclononaphan-9-one

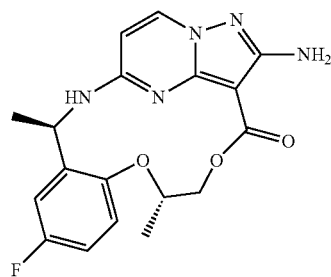 [SMILES: C[C@H]1COC(=O)c2c(N)nn3ccc(nc23)N[C@H](C)c2cc(F)ccc2O1]

Example 19:
(1³Z,1⁴E,3R,6S)-1²-bromo-4⁵-fluoro-3,6-dimethyl-5,8-dioxa-2-aza-1(5,3)-pyrazolo[1,5-a]pyrimidina-4(1,2)-benzenacyclononaphan-9-one

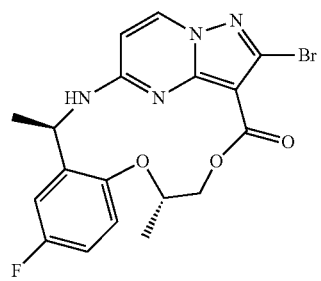 [SMILES: C[C@H]1COC(=O)c2c(Br)nn3ccc(nc23)N[C@H](C)c2cc(F)ccc2O1]

Example 20:
(1³E,1⁴E,3R,6S)-4⁵-fluoro-3,6-dimethyl-9-oxo-5,8-dioxa-2-aza-1(5,3)-pyrazolo[1,5-a]pyrimidina-4(1,2)-benzenacyclononaphane-12-carbonitrile

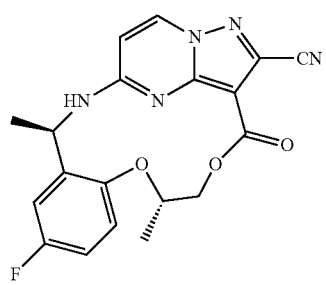 [SMILES: C[C@H]1COC(=O)c2c(C#N)nn3ccc(nc23)N[C@H](C)c2cc(F)ccc2O1]

Example 21:
(1³E,1⁴E,2²R,6R)-3⁵-fluoro-6-methyl-7-oxa-1(5,3)-pyrazolo[1,5-a]pyrimidina-3(3,2)-pyridina-2(1,2)-pyrrolidinacyclooctaphan-8-one

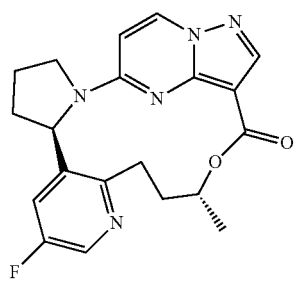 [SMILES: C[C@@H]1CCc2ncc(F)cc2[C@H]2CCCN2c2ccn3ncc(c3n2)C(=O)O1]

Example 22:
(R,1³E,1⁴E,7E)-4⁵-fluoro-3-methyl-5-oxa-2-aza-1(5,3)-pyrazolo[1,5-a]pyrimidina-4(1,2)-benzenacyclononaphan-7-en-9-one

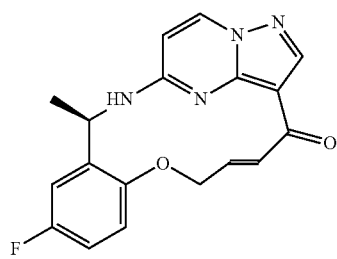 [SMILES: C[C@H]1Nc2ccn3ncc(c3n2)C(=O)/C=C/COc2ccc(F)cc21]

Example 6: (1³E,1⁴E,3R,7R)-4⁵-fluoro-3,7-dimethyl-5,8-dioxa-2-aza-1(5,3)-pyrazolo[1,5-a]pyrimidina-4(1,2)-benzenacyclononaphan-9-one

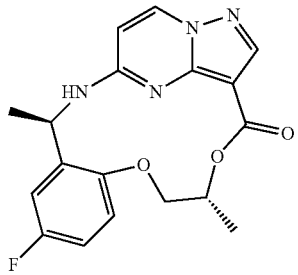 [SMILES: C[C@@H]1COc2ccc(F)cc2[C@@H](C)Nc2ccn3ncc(c3n2)C(=O)O1]

Step A: (R)-2-hydroxypropyl 4-methylbenzenesulfonate

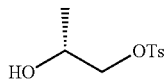

To a solution of (R)-propane-1,2-diol (2.08 g, 27.3 mmol, 1.0 eq) and Et₃N (8.3 g, 81.9 mmol, 3.0 eq) in 40 mL CH₂Cl₂, 4-methylbenzenesulfonyl chloride (5.2 g, 27.34 mmol, 1.0 eq) was slowly added at room temperature. Catalytic quantity of DMAP was added. The reaction was stirred overnight at room temperature. After adding water, the product was extracted three times with CH₂Cl₂, and washed once with saturated brine. The organic phases were dried over anhydrous Na₂SO₄ and evaporated in vacuum. The residue was purified by column chromatography on silica to yield the pure product (2.1 g, 33% yield).

¹H NMR (400 MHz, CDCl₃) δ 7.85 (d, J=8.2 Hz, 2H), 7.40 (d, J=8.0 Hz, 2H), 4.16-3.98 (m, 2H), 3.92-3.87 (m, 1H), 2.50 (s, 3H), 1.20 (d, J=6.4 Hz, 3H).

Step B: ethyl 5-(((R)-1-(5-fluoro-2-((R)-2-hydroxypropoxy)phenyl)ethyl)amino) pyrazolo[1,5-a]pyrimidine-3-carboxylate

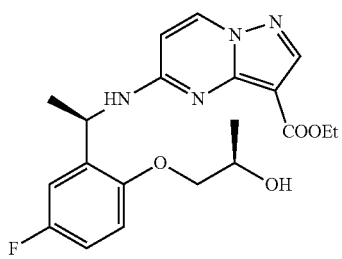 [SMILES: CCOC(=O)c1cnn2ccc(N[C@H](C)c3cc(F)ccc3OC[C@@H](C)O)nc12]

To a solution of ethyl (R)-5-((1-(5-fluoro-2-hydroxyphenyl)ethyl)amino) pyrazolo[1,5-a]pyrimidine-3-carboxylate (680 mg, 1.97 mmol, 1.0 eq) in DMF, K₂CO₃ (1.36 g, 9.85 mmol, 5.0 eq) and (R)-2-hydroxypropyl 4-methylbenzenesulfonate (500 mg, 2.17 mmol, 1.1 eq) was added in turn. After adding, the reaction mixture was heated to 80° C. at oil bath for 4 hours. After cooling to room temperature, the reaction was quenched with water, the product was extracted three times with EA. The combined organic phases were washed three times with water, dried over anhydrous Na₂SO₄ and evaporated in vacuum. The residue was purified by column chromatography on silica to yield the pure product (278 mg, 35% yield). LC-MS: m/z=403 [M+H]⁺.
LC-MS: m/z=403 [M+H]⁺.

Step C: 5-(((R)-1-(5-fluoro-2-((R)-2-hydroxypropoxy)phenyl)ethyl)amino) pyrazolo[1,5-a]pyrimidine-3-carboxylic acid

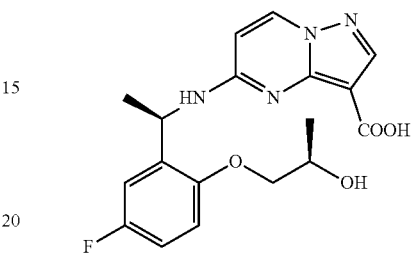

Procedure referred to step C of example 13.
LC-MS: m/z=375 [M+H]⁺.

Step D: (1³E,1⁴E,3R,7R)-4s-fluoro-3,7-dimethyl-5,8-dioxa-2-aza-1(5,3)-pyrazolo[1,5-a]pyrimidina-4(1,2)-benzenacyclononaphan-9-one

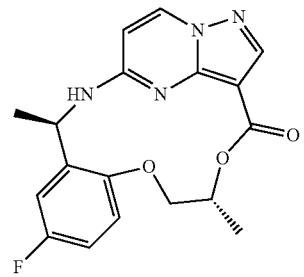 [SMILES: C[C@@H]1COc2ccc(F)cc2[C@@H](C)Nc2ccn3ncc(c3n2)C(=O)O1]

Procedure referred to step D of example 13.
¹H NMR (400 MHz, CDCl₃) δ 8.24 (s, 1H), 8.18 (d, J=7.2 Hz, 1H), 7.01 (d, J=9.0 Hz, 1H), 6.88-6.86 (m, 1H), 6.79 (s, 1H), 6.17-6.15 (m, 2H), 5.62 (s, 1H), 5.52 (s, 1H), 4.37 (d, J=10.4 Hz, 1H), 4.08 (d, J=10.0 Hz, 1H), 1.71 (d, J=6.4 Hz, 3H), 1.57 (d, J=7.0 Hz, 3H). LC-MS: m/z=357 [M+H]⁺.

Example 9: (1³E,1⁴E,3R,6S)-4⁵-fluoro-3,6-dimethyl-8-oxa-5-thia-2-aza-1(5,3)-pyrazolo[1,5-a]pyrimidina-4(1,2)-benzenacyclononaphan-9-one

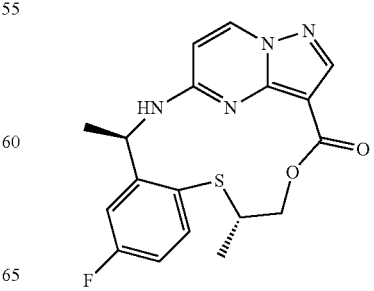

Step A: ethyl (R)-5-((1-(5-fluoro-2-(((trifluoromethyl)sulfonyl)oxy) phenyl)ethyl)amino)pyrazolo[1,5-a]pyrimidine-3-carboxylate

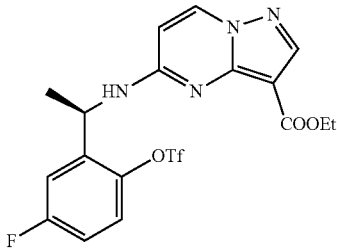 [SMILES: CCOC(=O)c1cnn2ccc(N[C@H](C)c3cc(F)ccc3OS(=O)(=O)C(F)(F)F)nc12]

To a solution of ethyl (R)-5-((1-(5-fluoro-2-hydroxyphenyl)ethyl)amino)pyrazolo[1,5-a]pyrimidine-3-carboxylate in CH$_2$Cl$_2$ under an ice bath, pyridine (489 mg, 3.18 mmol, 3.0 eq) and trifluoromethanesulfonic anhydride (872 mg, 3.09 mmol, 1.5 eq) were slowly added in turn. The reaction was stirred for 2 hours at room temperature. After adding water, the product was extracted three times with CH$_2$Cl$_2$. The combined organic phases were washed once with saturated brine, dried over anhydrous Na$_2$SO$_4$ and evaporated in vacuum. The residue was purified by column chromatography on silica to yield the pure product (785 mg, 80% yield).

LC-MS: m/z=477 [M+H]$^+$.

Step B: (R)-1-((tert-butyldimethylsilyl)oxy)propan-2-yl 4-methylbenzenesulfonate

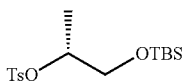

Procedure referred to step A of example 6.

Step C: (S)—S-(1-((tert-butyldimethylsilyl)oxy)propan-2-yl) ethanethioate

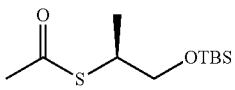

To a solution of (S)—S-(1-((tert-butyldimethylsilyl)oxy)propan-2-yl) ethanethioate (2.0 g, 5.8 mmol, 1.0 eq) in DMF, potassium ethanethioate (796 mg, 6.96 mmol, 1.2 eq) was slowly added. The reaction mixture was heated to 60° C. at oil bath for 4 hours. After cooling to RT, water was added. The product was extracted three times with EA. The combined organic phases were washed three times with water, dried over anhydrous Na$_2$SO$_4$ and evaporated in vacuum. The residue was purified by column chromatography on silica to yield the pure product (1.0 g, 69% yield).

Step D: (S)-1-((tert-butyldimethylsilyl)oxy)propane-2-thiol

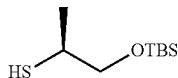

To a solution of (S)—S-(1-((tert-butyldimethylsilyl)oxy)propan-2-yl)ethanethioate (1.0 g, 4.02 mmol, 1.0 eq) in MeOH/H$_2$O (5:1), NaOH (241 mg, 6.03 mmol, 1.5 eq) was slowly added under an ice bath. The reaction was stirred for further 0.5 hours. MeOH was removed via vacuum distillation, and the product was extracted three times with CH$_2$C2. The combined organic phases were washed once with water, dried over anhydrous Na$_2$SO$_4$ and evaporated in vacuum. The residue was purified by column chromatography on silica to yield the pure product (700 mg, 84% yield).

Step E: ethyl 5-(((R)-1-(2-(((S)-1-((tert-butyldimethylsilyl)oxy)propan-2-yl)thio)-5-fluorophenyl)ethyl)amino)pyrazolo[1,5-a]pyrimidine-3-carboxylate

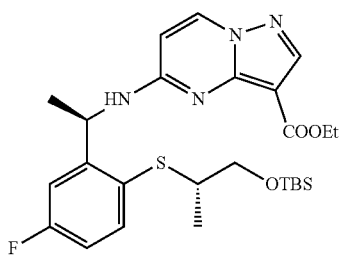 [SMILES: CCOC(=O)c1cnn2ccc(N[C@H](C)c3cc(F)ccc3S[C@@H](C)CO[Si](C)(C)C(C)(C)C)nc12]

To a solution of ethyl (R)-5-((1-(5-fluoro-2-(((trifluoromethyl) sulfonyl)oxy)phenyl) ethyl)amino)pyrazolo[1,5-a]pyrimidine-3-carboxylate (646 mg, 1.35 mmol, 1.0 eq) in 1,4-dioxane, (S)-1-((tert-butyldimethylsilyl)oxy)propane-2-thiol (700 mg, 3.39 mmol, 2.5 eq), Xantphos (156 mg, 0.27 mmol, 0.2 eq), DIEA (1.3 mL, 8.1 mmol, 6.0 eq) and Pd$_2$(dba)$_3$ (124 mg, 0.135 mmol, 0.1 eq) were added. It was replaced 3 times with N$_2$, and heated to 120° C. overnight via oil bath. After cooling to RT, water was added. The product was extracted 3 times with EA. The combined organic phases were washed once with saturated water, dried over anhydrous Na$_2$SO$_4$ and evaporated in vacuum. The residue was purified by column chromatography on silica to yield the pure product (390 g, 54% yield).

LC-MS: m/z=533 [M+H]$^+$.

Step F: ethyl 5-(((R)-1-(5-fluoro-2-(((S)-1-hydroxy-propan-2-yl)thio)phenyl) ethyl)amino)pyrazolo[1,5-a]pyrimidine-3-carboxylate

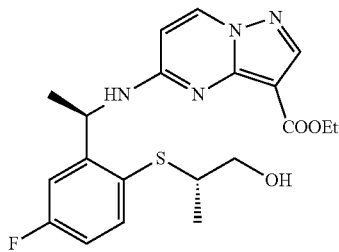 [SMILES: CCOC(=O)c1cnn2ccc(N[C@H](C)c3cc(F)ccc3S[C@@H](C)CO)nc12]

Procedure referred to step B of example 13.
LC-MS: m/z=419 [M+H]+.

Step G: 5-(((R)-1-(5-fluoro-2-(((S)-1-hydroxypropan-2-yl)thio)phenyl)ethyl)amino) pyrazolo[1,5-a] pyrimidine-3-carboxylic acid

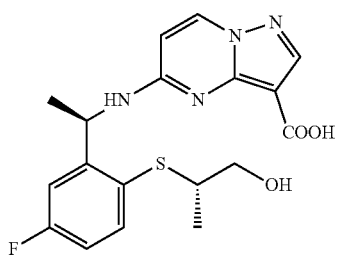 [SMILES: C[C@@H](CO)Sc1ccc(F)cc1[C@@H](C)Nc1ccn2ncc(C(=O)O)c2n1]

Procedure referred to step C of example 13.
LC-MS: m/z=391 [M+H]+.

Step H: ($1^3$E,$1^4$E,3R,6S)-$4^5$-fluoro-3,6-dimethyl-8-oxa-5-thia-2-aza-1 (5,3)-pyrazolo[1,5-a]pyrimidina-4(1,2)-benzenacyclononaphan-9-one

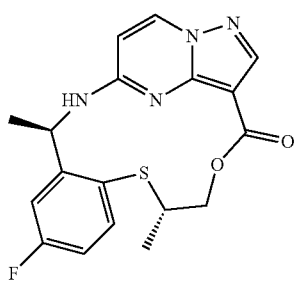 [SMILES: C[C@H]1COC(=O)c2cnn3ccc(nc23)N[C@H](C)c2cc(F)ccc2S1]

Procedure referred to step D of example 13.
$^1$H NMR (400 MHz, CDCl$_3$) δ 8.36-8.24 (m, 2H), 7.49-7.47 (m, 1H), 7.13-6.94 (m, 2H), 6.28 (d, J=7.6 Hz, 1H), 6.12-6.01 (m, 1H), 5.66 (s, 1H), 5.03 (dd, J=11.6, 3.8 Hz, 1H), 3.87 (t, J=11.2 Hz, 1H), 3.50-3.49 (m, 1H), 1.74 (d, J=7.2 Hz, 3H), 1.50 (d, J=7.0 Hz, 3H).
LC-MS: m/z=373 [M+H]+.

Example 13: (R,$1^3$E,$1^4$E)-$4^5$-fluoro-3-methyl-5,8-dioxa-2-aza-1(5,3)-pyrazolo[1,5-a]pyrimidina-4(1,2)-benzenacyclononaphan-9-one

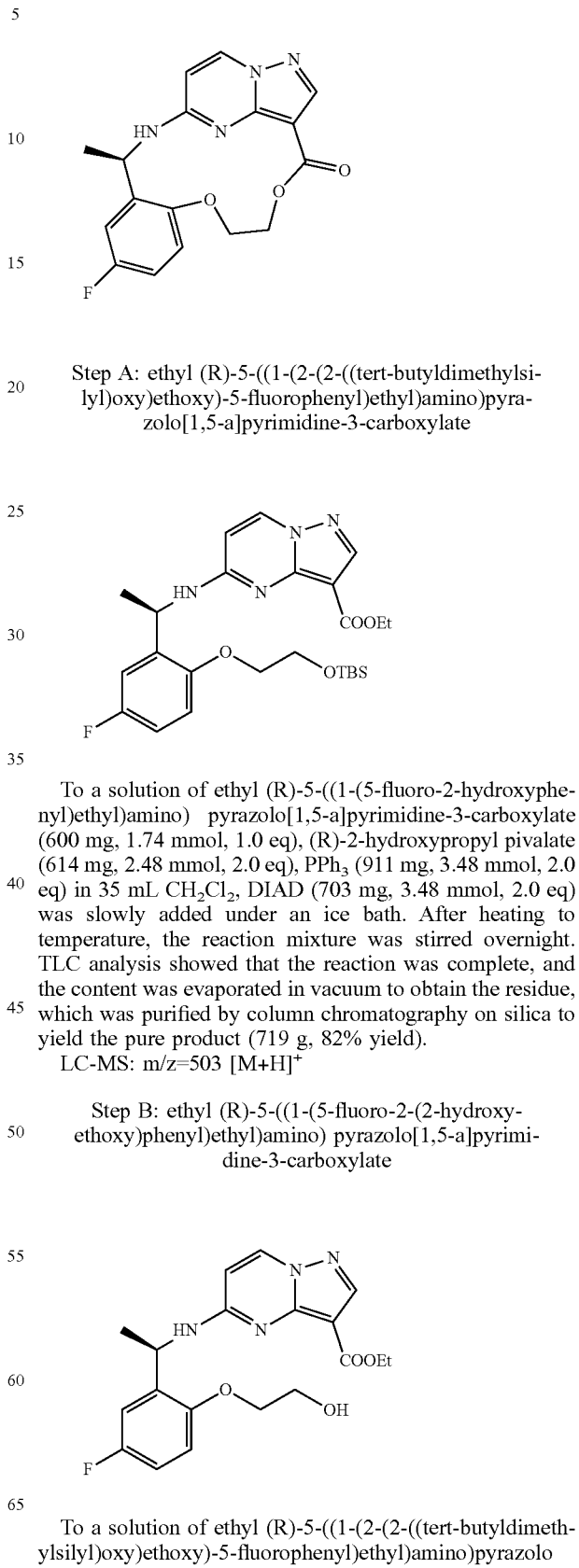

Step A: ethyl (R)-5-((1-(2-(2-((tert-butyldimethylsilyl)oxy)ethoxy)-5-fluorophenyl)ethyl)amino)pyrazolo[1,5-a]pyrimidine-3-carboxylate To a solution of ethyl (R)-5-((1-(5-fluoro-2-hydroxyphenyl)ethyl)amino) pyrazolo[1,5-a]pyrimidine-3-carboxylate (600 mg, 1.74 mmol, 1.0 eq), (R)-2-hydroxypropyl pivalate (614 mg, 2.48 mmol, 2.0 eq), PPh$_3$ (911 mg, 3.48 mmol, 2.0 eq) in 35 mL CH$_2$Cl$_2$, DIAD (703 mg, 3.48 mmol, 2.0 eq) was slowly added under an ice bath. After heating to temperature, the reaction mixture was stirred overnight. TLC analysis showed that the reaction was complete, and the content was evaporated in vacuum to obtain the residue, which was purified by column chromatography on silica to yield the pure product (719 g, 82% yield).
LC-MS: m/z=503 [M+H]+

Step B: ethyl (R)-5-((1-(5-fluoro-2-(2-hydroxyethoxy)phenyl)ethyl)amino) pyrazolo[1,5-a]pyrimidine-3-carboxylate To a solution of ethyl (R)-5-((1-(2-(2-((tert-butyldimethylsilyl)oxy)ethoxy)-5-fluorophenyl)ethyl)amino)pyrazolo

[1,5-a]pyrimidine-3-carboxylate (719 mg, 1.43 mmol, 1.0 eq) in THF, tetrabutylammonium fluoride trihydrate (900 mg, 2.86 mmol, 2.0 eq) was added under an ice bath. After adding and heating to room temperature, the reaction was stirred for further 1.5 hours at room temperature. After adding water, the product was extracted 3 times with EA. The combined organic phases were washed once with water, dried over anhydrous Na$_2$SO$_4$ and concentrated via vacuum distillation. The residue was purified by column chromatography on silica to yield the pure product (519 mg, 93% yield).

LC-MS: m/z=389 [M+H]$^+$.

Step C: (R)-5-((1-(5-fluoro-2-(2-hydroxyethoxy) phenyl)ethyl)amino)pyrazolo[1,5-a]pyrimidine-3-carboxylic acid

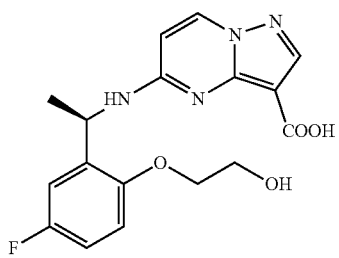 [SMILES: C[C@@H](Nc1ccn2ncc(C(=O)O)c2n1)c1cc(F)ccc1OCCO]

To a solution of ethyl (R)-5-((1-(5-fluoro-2-(2-hydroxyethoxy)phenyl)ethyl) amino)pyrazolo[1,5-a]pyrimidine-3-carboxylate (519 mg, 1.34 mmol, 1.0 eq) in MeOH/H$_2$O (5:1) was added NaOH (1.6 g, 40.2 mmol, 40.0 eq) and heated to 80° C. for 5.0 hour under oil bath. The solution was cooled to room temperature, partially concentrated via vacuum distillation, and acidified with 1N HCl solution until pH 5. The resulting suspension was extracted twice with EtOAc. The combined organic layers were dried over anhydrous Na$_2$SO$_4$ and evaporated in vacuum to obtain the product. (482 mg, 100% yield).

LC-MS: m/z=361 [M+H]$^+$.

Step D: (R,1$^3$E,1$^4$E)-4$^5$-fluoro-3-methyl-5,8-dioxa-2-aza-1(5,3)-pyrazolo[1,5-a]pyrimidina-4(1,2)-benzenacyclononaphan-9-one

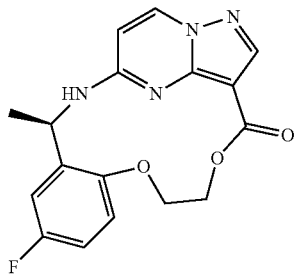 [SMILES: C[C@H]1Nc2ccn3ncc(c3n2)C(=O)OCCOc2ccc(F)cc21]

To a solution of (R)-5-((1-(5-fluoro-2-(2-hydroxyethoxy) phenyl)ethyl) amino)pyrazolo[1,5-a]pyrimidine-3-carboxylic acid (150 mg, 0.42 mmol, 1.0 eq) and 1-ethyl-(3-dimethylaminopropyl)carbodiimide hydrochloride (161 mg, 0.84 mmol, 2.0 eq) in DCM was added 4-dimethylaminopyridine (DMAP) (5 mg, 0.1 eq). The mixture was heated via oil bath to reflux for 5.0 hour. After cooling to RT, water was added. The resulting suspension was extracted 3 times with DCM. The combined extracts were washed once with saturated brine, dried with anhydrous Na$_2$SO$_4$ and concentrated under reduced pressure. The residue was purified by column chromatography on silica to yield the pure product (60 mg, 42% yield).

$^1$H NMR (400 MHz, CDCl$_3$) δ 8.26 (s, 1H), 8.20 (d, J=7.4 Hz, 1H), 7.04 (dd, J=9.0, 2.6 Hz, 1H), 6.95-6.78 (m, 2H), 6.21 (d, J=7.4 Hz, 1H), 6.14-6.01 (m, 1H), 5.85 (d, J=5.9 Hz, 1H), 5.06 (d, J=11.8 Hz, 1H), 4.62-4.59 (m, 1H), 4.49-4.45 (m, 1H), 4.39-4.19 (m, 2H), 1.56 (d, J=7.0 Hz, 3H). LC-MS: m/z=343 [M+H]$^+$.

Example 23: (R,1$^3$E,1$^4$E)-4$^5$-fluoro-2,3-dimethyl-5,8-dioxa-2-aza-1(5,3)-pyrazolo[1,5-a]pyrimidina-4(1,2)-benzenacyclononaphan-9-one

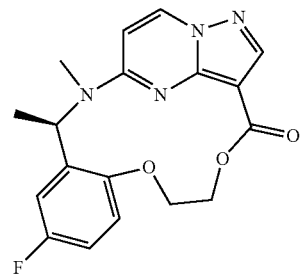 [SMILES: C[C@@H]1c2cc(F)ccc2OCCOC(=O)c2cnn3ccc(nc23)N1C]

Step A: tert-butyl (R)-(1-(5-fluoro-2-hydroxyphenyl)ethyl)carbamate

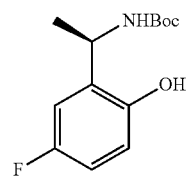 [SMILES: C[C@@H](NC(=O)OC(C)(C)C)c1cc(F)ccc1O]

To a solution of (R)-2-(1-aminoethyl)-4-fluorophenol hydrochloride (3.7 g, 19.3 mmol, 1.0 eq) and trimethylamine (TEA) (5.4 mL, 38.6 mmol, 2.0 eq) in DCM was added di-tert-butyl dicarbonate (Boc$_2$O) (4.6 g, 21.2 mmol, 1.1 eq). After adding, the mixture was stirred at rt for 2 hours. The reaction mixture was concentrated under reduced pressure. The residue was purified by column chromatography on silica to yield the product (4.9 g, 100% yield).

LC-MS: m/z=256 [M+H]$^+$.

Step B: tert-butyl (R)-(1-(2-(2-((tert-butyldimethylsilyl)oxy)ethoxy)-5-fluorophenyl) ethyl)carbamate

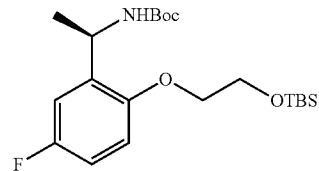 [SMILES: C[C@@H](NC(=O)OC(C)(C)C)c1cc(F)ccc1OCCO[Si](C)(C)C(C)(C)C]

To a solution of (600 mg, 2.35 mmol, 1.0 eq) and K$_2$CO$_3$ (1.3 g, 9.4 mmol, 4.0 eq) in DMF was added (2-bromoethoxy)(tert-butyl)dimethylsilane(1.1 g, 4.7 mmol, 2.0 eq) and heated to 80° C. under oil bath for 4.0 hour. The mixture was cooled to RT. After adding water, the mixture was extracted 3 times with ethyl acetate. The combined organic layers were washed 3 times with water, and dried with anhydrous Na$_2$SO$_4$ and concentrated under reduced pressure. The residue was purified by column chromatography on silica to yield the product (670 mg, 69% yield).

LC-MS: m/z=414 [M+H]$^+$.

Step C: tert-butyl (R)-(1-(2-(2-((tert-butyldimethylsilyl)oxy)ethoxy)-5-fluorophenyl) ethyl)(methyl)carbamate

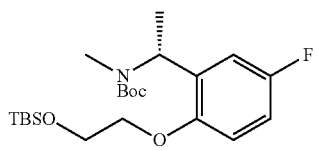 [SMILES: C[C@H](c1cc(F)ccc1OCCO[Si](C)(C)C(C)(C)C)N(C)C(=O)OC(C)(C)C]

To a solution of (670 mg, 1.62 mmol, 1.0 eq) in DMF was added NaH (194 mg, 4.86 mmol, 3.0 eq) under ice bath. After adding, the mixture was stirred at the temperature for 15 min and was added CH$_3$I (460 mg, 3.24 mmol, 2.0 eq). The reaction was performed for further 2h. After adding water, the mixture was extracted 3 times with ethyl acetate. The combined organic layers were washed 3 times with water, and dried with anhydrous Na$_2$SO$_4$ and concentrated under reduced pressure. The residue was purified by column chromatography on silica to yield the product (692 mg, 100% yield).

LC-MS: m/z=428 [M+H]$^+$.

Step D: tert-butyl (R)-(1-(5-fluoro-2-(2-hydroxyethoxy)phenyl)ethyl)(methyl)carbamate

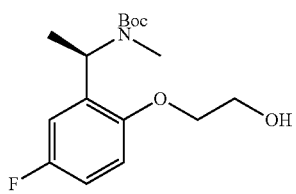 [SMILES: C[C@H](c1cc(F)ccc1OCCO)N(C)C(=O)OC(C)(C)C]

Procedure referred to step B of example 13.
$^1$H NMR (400 MHz, CDCl$_3$) δ 7.12-6.94 (m, 2H), 6.84-6.80 (m Hz, 1H), 5.92 (bRs, 1H), 4.63 (bRs, 1H), 4.15-4.13 (m, 1H), 3.92-3.88 (m, 3H), 2.55 (s, 3H), 1.53 (s, 9H), 1.46 (d, J=7.0 Hz, 3H). LC-MS: m/z=314 [M+H]$^+$.

Step E: (R)-2-(4-fluoro-2-(1-(methylamino)ethyl)phenoxy)ethan-1-ol

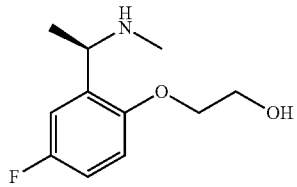

Procedure referred to step C of example 24.
LC-MS: m/z=214 [M+H]$^+$.

Step F: ethyl (R)-5-((1-(5-fluoro-2-(2-hydroxyethoxy)phenyl)ethyl)(methyl)amino)pyrazolo[1,5-a]pyrimidine-3-carboxylate Procedure referred to step D of example 1.
LC-MS: m/z=403 [M+H]$^+$.

Step G: (R)-5-((1-(5-fluoro-2-(2-hydroxyethoxy)phenyl)ethyl)(methyl)amino)pyrazolo[1,5-a]pyrimidine-3-carboxylic acid

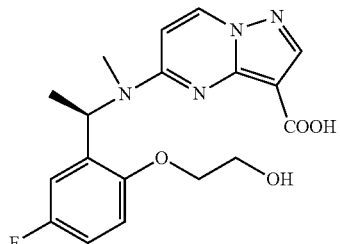

Procedure referred to step C of example 13.
LC-MS: m/z=375 [M+H]$^+$.

Step H: (R,1$^3$E,1$^4$E)-4$^5$-fluoro-2,3-dimethyl-5,8-dioxa-2-aza-1(5,3)-pyrazolo[1,5-a]pyrimidina-4(1,2)-benzenacyclononaphan-9-one

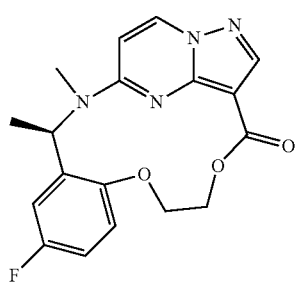 [SMILES: C[C@@H]1c2cc(F)ccc2OCCOC(=O)c2cnn3ccc(nc23)N1C]

Procedure referred to step D of example 13.
$^1$H NMR (400 MHz, CDCl$_3$) δ 8.39-8.25 (m, 2H), 7.01-6.69 (m, 4H), 6.42 (d, J=7.8 Hz, 1H), 5.0-5.07 (m, 1H), 4.58-5.56 (m, 1H), 4.44-4.42 (m, 1H), 4.17-4.15 (m, 1H), 3.43 (s, 3H), 1.62 (d, J=7.4 Hz, 3H). LC-MS: m/z=357 [M+H]$^+$.

Example 24: (R,1³E,1⁴E)-4⁵,6,6-trifluoro-3-methyl-5,8-dioxa-2-aza-1(5,3)-pyrazolo[1,5-a]pyrimidina-4(1,2)-benzenacyclononaphan-9-one

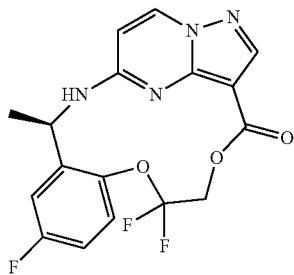 [SMILES: C[C@H]1Nc2ccn3ncc(c3n2)C(=O)OCC(F)(F)Oc2ccc(F)cc21]

Step A: ethyl (R)-2-(2-(1-((tert-butoxycarbonyl)amino)ethyl)-4-fluorophenoxy)-2,2-difluoroacetate

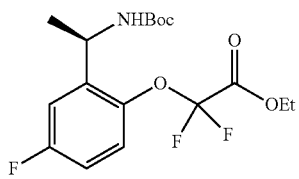 [SMILES: CCOC(=O)C(F)(F)Oc1ccc(F)cc1[C@@H](C)NC(=O)OC(C)(C)C]

To a solution of (700 mg, 2.75 mmol, 1.0 eq) and ethyl 2-bromo-2,2-difluoroacetate (1.4 g, 6.86 mmol, 2.5 eq) in DMF was added DBU (1.06 g, 6.86 mmol, 2.5 eq) and heated to 70° C. under oil bath for 4.0 hour. The mixture was cooled to RT. After adding water, the mixture was extracted 3 times with ethyl acetate. The combined organic layers were washed 3 times with saturated brine, and dried with anhydrous Na₂SO₄ and concentrated under reduced pressure. The residue was purified by column chromatography on silica to yield the product (720 mg, 69% yield).

$^1$H NMR (400 MHz, CDCl₃) δ 7.33-7.23 (m, 1H), 7.10-7.07 (m, 1H), 6.97-5.93 (m, 1H), 5.19 (s, 1H), 4.98 (s, 1H), 4.45 (q, J=7.0 Hz, 2H), 1.49-1.39 (m, 15H).

Step B: tert-butyl (R)-(1-(2-(1,1-difluoro-2-hydroxyethoxy)-5-fluorophenyl)ethyl) carbamate

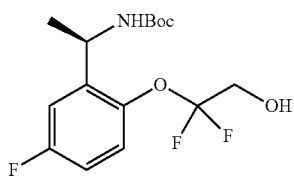 [SMILES: C[C@@H](NC(=O)OC(C)(C)C)c1cc(F)ccc1OC(F)(F)CO]

To a solution of ethyl (R)-2-(2-(1-((tert-butoxycarbonyl)amino)ethyl)-4-fluoro phenoxy)-2,2-difluoroacetate (720 mg, 1.9 mmol, 1.0 eq) in THF was added lithium aluminum hydride (160 mg, 4.2 mmol, 2.2 eq) under ice bath. The mixture was stirred at 0° C. for 2 hours. The reaction was quenched by adding water. The mixture was extracted 3 times with ethyl acetate. The combined organic layers were washed 3 times with saturated brine, and dried with anhydrous Na₂SO₄ and concentrated under reduced pressure. The residue was purified by column chromatography on silica to yield the product (450 mg, 71% yield).

$^1$H NMR (400 MHz, CDCl₃) δ 7.36-7.33 (m, 1H), 7.14-6.94 (m, 2H), 5.27 (s, 1H), 4.87 (bRs, 2H), 4.05-3.97 (m, 2H), 1.51-1.41 (m, 12H).

Step C: (R)-2-(2-(1-aminoethyl)-4-fluorophenoxy)-2,2-difluoroethane-1-ol

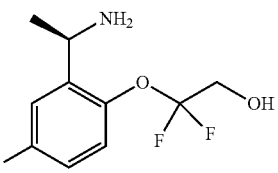

To a solution of (450 mg, 1.34 mmol, 1.0 eq) in DCM was added 4 mL trifluoroacetic acid (TFA). The mixture was stirred for 3 hours. Saturated sodium bicarbonate solution was added until it was alkaline. The mixture was extracted 3 times with ethyl acetate. The combined extracts were dried with anhydrous Na₂SO₄ and concentrated under reduced pressure to yield the product (315 mg, 100% yield).

LC-MS: m/z=236 [M+H]⁺.

Step D: ethyl (R)-5-((1-(2-(1,1-difluoro-2-hydroxyethoxy)-5-fluorophenyl) ethyl) amino)pyrazolo[1,5-a]pyrimidine-3-carboxylate

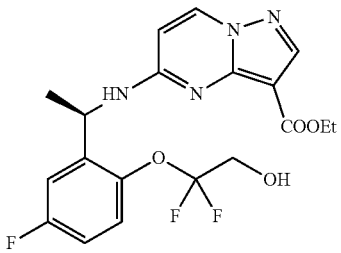 [SMILES: CCOC(=O)c1cnn2ccc(N[C@H](C)c3cc(F)ccc3OC(F)(F)CO)nc12]

Procedure referred to step D of example 1.
LC-MS: m/z=425 [M+H]+.

Step E: (R)-5-((1-(2-(1,1-difluoro-2-hydroxyethoxy)-5-fluorophenyl)ethyl)amino) pyrazolo[1,5-a]pyrimidine-3-carboxylic acid

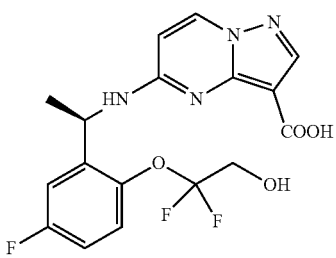 [SMILES: C[C@@H](Nc1ccn2ncc(C(=O)O)c2n1)c1cc(F)ccc1OC(F)(F)CO]

Procedure referred to step C of example 13.
LC-MS: m/z=397 [M+H]+.

Step F: (R,1³E,1⁴E)-4⁵,6,6-trifluoro-3-methyl-5,8-dioxa-2-aza-1(5,3)-pyrazolo[1,5-a]pyrimidina-4(1,2)-benzenacyclononaphan-9-one

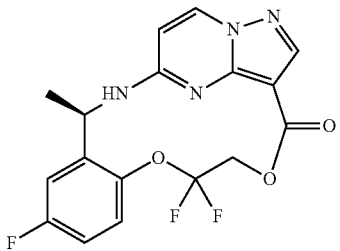 [SMILES: C[C@H]1Nc2ccn3ncc(c3n2)C(=O)OCC(F)(F)Oc2ccc(F)cc21]

Procedure referred to step D of example 13.

¹H NMR (400 MHz, CDCl₃) δ 8.27-8.25 (m, 2H), 7.23 (s, 1H), 7.08 (dd, J=8.8, 3.0 Hz, 1H), 6.94-6.90 (m, 1H), 6.26 (d, J=7.5 Hz, 1H), 5.85 (bRs, 1H), 5.57 (bRs, 1H), 5.01-4.93 (m, 1H), 4.82-4.77 (m, 1H), 1.58 (d, J=7.0 Hz, 3H). LC-MS: m/z=379 [M+H]+.

Example 25: (R,1³E,1⁴E)-4⁵-fluoro-3-methyl-8-oxa-5-thia-2-aza-1(5,3)-pyrazolo[1,5-a]pyrimidina-4(1,2)-benzenacyclononaphan-9-one

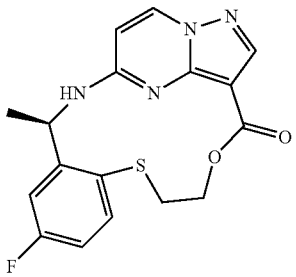 [SMILES: C[C@H]1Nc2ccn3ncc(c3n2)C(=O)OCCSc2ccc(F)cc21]

The compound was synthesised according to example 9.

¹H NMR (400 MHz, CDCl₃) δ 8.33-8.20 (m, 2H), 7.44-7.42 (m, 1H), 7.06-7.04 (m, 1H), 6.96-6.94 (m, 1H), 6.25 (d, J=7.4 Hz, 1H), 6.17-5.98 (m, 1H), 5.64 (s, 1H), 5.02-5.00 (m, 1H), 4.21-4.06 (m, 1H), 3.78-3.76 (m, 1H), 3.33-3.18 (m, 1H), 1.49 (d, J=7.0 Hz, 3H). LC-MS: m/z=359 [M+H]+.

Compound Evaluation

1. Inhibitory Activity of Compounds on TRKA, TRKB, TRKC and ROS1 (IC₅₀)

The inhibitory activity of compounds on TRKA, TRKB, TRKC and ROS1 kinase was analyzed with Mobility shift assay. The screening platform is MSA based microfluidic chip technology, which applies the basic concept of capillary electrophoresis to microfluidic environment. The substrate used in the experiment is a poly-peptide labeled with fluorescent. Under the catalysis of enzyme in the reaction system, the substrate is transformed into a product, with the charge changed accordingly. MSA technology could detect the substrate and the product with different charge separately.

The operation is described as follows:

The compound powder was dissolved in 100% DMSO (Sigma, Cat. D8418-11) to prepare a 10 mM storage solution. The compounds had an initial test concentration of 100 nM, were 3-fold serially diluted to obtain 10 samples for multiple hole inspection. For TRKA, TRKB and TRKC kinase targets, Loxo-101 (Selleckchem, Cat. S7960) was used as positive reference compound; for ROS1, Staurosporine (Selleckchem, Cat. S1421) was used as positive reference compound. The gradient diluted compounds were mixed with TRKA/TRKB/TRKC/ROS1 kinase (Carna, Cat. 08-186/08-187/08-197/08-163) with final concentration of 2.5 nM/2.55 nM/2.5 nM/0.3 nM in a Optiplate-384F plate (PerkinElmer, Cat. 6007270), and incubated at room temperature for 10 minutes. After that, ATP was added with final concentration of 47.8 μM/71.2 μM/44.4 μM/26.7 μM, 3 μM Kinase Substrate22 (GL Biochem, Cat. 112393) was added. The reaction was carried out at room temperature for 30 min/40 min/20 min/20 min respectively. After the reaction was terminated, the conversion rate was read by Caliper EZ Reader II.

Data Analysis:

$$\% \text{ Inhibition} = \frac{\text{Conversion \%\_max} - \text{Conversion \%\_sample}}{\text{Conversion \%\_max} - \text{Conversion \%\_min}} \times 100$$

Conversion %_Sample: conversion rate of sample;
Conversion %_Min: mean value of negative control, representing the conversion rate without enzyme activity;
Conversion %_Max: mean value of positive control, which represents the conversion rate reading without compound inhibition.

Taking the log value of concentration as X axis and the percentage inhibition rate as Y axis, the dose response curve was fitted by the analysis software GraphPad Prism 5, thus the IC₅₀ value of each compound on enzyme activity inhibition was obtained.

2. Inhibitory Activity of Compounds to ROS1-G2032R (IC₅₀)

Based on LanceUltra (Perkin Elmer, CR97-100) principle, ROS1-G2032R kinase activity detection platform was established to determine the inhibitory activity of compounds.

The compound powder was dissolved in 100% DMSO (Sigma, Cat. D8418-11) to prepare a 10 mM storage solution. The compounds had an initial test concentration of 1000 nM, were 3-fold serially diluted to obtain 11 samples for multiple hole inspection. TPX-0005 (WuXi AppTec. supplied) was used as positive reference compound. The gradient diluted compounds were mixed with 0.016 nM ROS1-G2032R kinase (Abcam, Cat. ab206012), 50 nM LANCE Ultra ULight-poly GT peptide (PerkinElmer, Cat. TRF0100-M) and 2.6 μM ATP (Sigma, Cat. A7699) in the Optiplate-384F plate (PerkinElmer, Cat. 6007299) and incubated at room temperature for 60 mins. 5 μl 40 mM EDTA was used to stop the reaction. Then 2 nM Europium-anti-phosphotyrosine (PT66) (PerkinElmer, Cat. AD0069) was added and incubated at room temperature for 60 mins. The LANCE signal was obtained by EnVision™ (PerkinElmer, 2014) (Excitation light, 320 nm; Emission light, 665 nm). The IC₅₀ values of the compounds were calculated using XLFIT5 (IDBS) software.

3. Inhibitory Activity of Compounds on TRKA and ALK-L1196M (IC₅₀)

Based on HTRF of Cisbio (Cisbio, Cat. 08-52) principle, TRKA and ALK-L1196M kinase activity detection platform were established to determine the inhibitory activity of compounds. The compound powder was dissolved in 100% DMSO (Sigma, Cat. D8418-11) to prepare a 10 mM storage solution. The compounds had an initial test concentration of 1000 nM and 10,000 nM respectively, were 3-fold serially diluted to obtain 11 samples for multiple hole inspection. RXDX-101 (WuXi AppTec. supplied) or Crizotinib (WuXi AppTec. Supplied) was used as positive reference compound.

The gradient diluted compounds were mixed with 0.5 nM TRKA (Carna, Cat. 08-186)/ALK-L1196M (Carna, Cat. 08-529), 0.3 µM/1 µM TK Substrate-biotin and 90 µM/30 µM ATP (Sigma, Cat. A7699) in a Optiplate-384F plate (PerkinElmer, Cat. 6007299) and incubated at room temperature for 90 mins/120 mins. Then 0.67 nM Eu-TK-Antibody and 50 nM Streptavidin-XL-665 were added, mixed and incubated at room temperature for 60 min. The fluorescence value was obtained by Envision (PerkinElmer, #2014) (Excitation light, 320 nm; Emission light, 665 nm). The $IC_{50}$ values of the compounds were calculated using XLFIT5 (IDBS) software.

4. Inhibitory Effect of Compounds on the Proliferation of TRK Fusion and Mutant Stable Cell Lines ($IC_{50}$)

Inhibitory effects of compounds on six cell lines were tested, while LOXO-101 (Selleckchem, Cat. S7960) and TPX-0005 (Selleckchem, Cat. S8583) were used as control compound. Six cell lines including Ba/F3 LMNA-NTRK1-WT, Ba/F3 LMNA-NTRK1-G595R, Ba/F3 ETV6-NTRK2-WT, Ba/F3 ETV6-NTRK2-G639R, Ba/F3 ETV6-NTRK2-G639R and Ba/F3 ETV6-NTRK3-G623R were used in this experiment. For the six cell lines, the maximum test concentration of the compound was 1 µM, 1 µM, 10 µM, 100 PM, 1 µM and 10 µM, were 3.16-fold gradient diluted to obtain 9 samples.

The operation is described briefly as follows:

The cells in logarithmic growth phase were harvested to ensure that the cell viability was above 90%. 3000 cell/well were seeded in 96-well plate (Corning, Cat #3603). The cells were incubated overnight with 5% $CO_2$, 95% humidity at 37° C. Then each well containing the cells of the 96-well plate was added the compound solutions, 3 wells for each compound solution, and continued to incubate for another 72 hrs. Then CellTiter-Glo® kit (Promega, Cat #G7572) was used to do the detection. First, the CTG reagent was melted and the cell plate was balanced to room temperature. The same volume of CTG solution was added into each well and vibrated on the shaker for 5 minutes to lyse the cells. The cell plate was kept at room temperature for 20 minutes to stabilize the luminescent signal. The luminescent value was collected by SpectraMax microplate detector (MD, 2104-0010A). The dose response curve was fitted by the analysis software GraphPad Prism 5, thus the $IC_{50}$ value of each compound on cell proliferation inhibition was obtained.

Cell survival rate (%)=($1um_{drug}-1um_{medium}$)/ ($1um_{cell}-1um_{medium}$)×100%

TABLE 1

Inhibitory activity on TRKA and ALK-L1196M kinases

| Compound | TRKA $IC_{50}$ (nM) | ALK L1196M $IC_{50}$ (nM) |
|---|---|---|
| Crizotinib | ND | 106 |
| Ceritinib | 182 | ND |
| Alectinib | 60.4 | ND |
| Lorlatinib | 6.2 | 9 |
| TPX-0005 | 0.067 | 39 |
| Example 1 | 0.13 | 50 |

TABLE 2

Inhibitory activity on TRKA, TRKB, TRKC, ROS1 and ROS1-G2032R kinases

| Compound | TRKA $IC_{50}$ (nM) | TRKB $IC_{50}$ (nM) | TRKC $IC_{50}$ (nM) | ROS1 $IC_{50}$ (nM) | ROS1-G2032R $IC_{50}$ (nM) |
|---|---|---|---|---|---|
| LOXO-101 | 1.1 | 1.9 | 2.0 | — | — |
| TPX-0005 | 0.32 | 0.44 | 0.55 | 0.17 | 1.01 |
| Example 1 | 0.42 | 0.50 | 0.61 | 0.33 | 0.36 |
| Example 13 | 0.62 | 0.90 | 0.73 | 1.9 | — |
| Example 6 | 0.75 | 1.20 | 1.20 | 0.78 | — |
| Example 23 | 0.39 | 0.48 | 0.63 | 4.8 | — |
| Example 24 | 0.56 | 0.60 | 0.75 | 0.29 | — |
| Example 9 | 0.59 | 0.86 | 0.76 | 0.54 | — |
| Example 25 | 1.10 | 1.60 | 1.10 | 1.20 | — |

TABLE 3

Inhibitory activity on proliferation of TRK fusion and mutant stable cell lines

| Cell line | $IC_{50}$ (nM) LOXO-101 | $IC_{50}$ (nM) TPX-0005 | TRKC Example 1 |
|---|---|---|---|
| Ba/F3 LMNA-NTRK1-WT | 47.4* | 0.7# | 5.4*/1.04 |
| Ba/F3 LMNA-NTRK1-G595R | 2174.3* | 2.0# | 7.8*/1.34 |
| Ba/F3 ETV6-NTRK2-WT | 75.3* | 2.5# | 7.8*/4.24 |
| Ba/F3 ETV6-NTRK2-G639R | 8183.5* | 86.6# | 100.5*/64.64 |
| Ba/F3 ETV6-NTRK3-WT | 6.8* | 0.8# | 0.2*/1.04 |
| Ba/F3 LMNA-NTRK3-G623R | 1095.7* | 9.0# | 8.4*/8.34 |

Note:
*the same batch of test;
the same batch of test.

5. Analysis of Synergistic Effect

H1975 (L858R and T790M double mutation) cells were cultured in RPMI-1640 medium containing 10% FBS and 1% P/S (promycin/streptomycin). In the testing of the compounds, H1975 cells were seeded in 96-well plate (Corning, Cat #3917) at 3000 cell/well and the compounds were added at 195 µL solution/well. The initial test concentration of the compound was 10 µM, 3-fold gradient diluted to obtain 11 samples. 4 µL of each sample was added to 96 µL RPMI-1640 medium to dilute the 25× Compound. 5 µL was added to 195 µL cell medium (the final concentration of DMSO is 0.1%, v/v). After 72 hr incubation, 35 µL of CellTiter-Blue® (Promega, Cat #G8082) was added to the cells. The fluorescence signal was measured with FlexStation 3 (Molecular Devices) according to the instructions, and the $IC_{50}$ value of the compound on cell proliferation inhibition was calculated by Graphpad Grism 5.0 software. The Chou-Talalay index method was used to analyze the effect of the combination. 0.9≤Combination Index (CI)≤1.1 means additive effect, 0.8≤CI<0.9 means low synergistic effect, 0.6≤CI<0.8 means medium synergistic effect, 0.4≤CI<0.6 means high synergistic effect, 0.2≤CI<0.4 means strong synergistic effect.

The data showed that the combination of example 1 and AZD9291 showed medium to high synergistic effect on the EGFR double mutant H1975 (L858R and T790M double mutation) cells (Example 1, CI=0.53-0.67), indicating that the combination of the test compound and the EGFR inhibitor may overcome EGFR resistance.

6. Pharmacokinetic Analysis

Male SD rats were grouped, each group having 3 rats. Each group was given the compound of Example 1 (5 mg/kg) or TPX-0005 (5 mg/kg) by single oral gavage, or the compound of Example 1 (1 mg/kg) by intravenous injection.

Animals were fasted overnight from 10 hours before administration to 4 hours after administration. Blood samples were collected at 0.25, 0.5, 1, 2, 4, 8 and 24 hours after administration in the oral group and at 0.083, 0.25, 0.5, 1, 2, 4, 8 and 24 hours after injection in the intravenous group. After isoflurane anesthesia, 0.3 ml whole blood collected through the fundus vein plexus was put into the heparin anticoagulant tube. The sample was centrifuged at 4° C. at 4000 rpm for 5 min. The plasma was transferred into the centrifuge tube and stored at −80° C. until analysis. The extract from the plasma extracted by protein precipitation was analyzed by LC/MS/MS. The PK results were shown in Table 4 and table 5.

TABLE 4

Rat PK analysis (PO, 5 mg/kg)

| | Example 1 | TPX-0005 |
|---|---|---|
| $T_{1/2}$ (hr) | 1.84 | 3.55 |
| Tmax (hr) | 0.667 | 1.33 |
| Cmax (ng/mL) | 952 | 503 |
| $AUC_{0-inf}$ (hr * ng/mL) | 3548 | 2948 |
| F (%) | 114 | 91.5 |

TABLE 5

Rat PK analysis (IV, 1 mg/kg)

| | Example 1 |
|---|---|
| $T_{1/2}$ (hr) | 1.70 |
| $C_0$ (ng/mL) | 217 |
| Vdss (L/kg) | 4.26 |
| Cl (mL/min/kg) | 27.2 |
| $AUC_{0-inf}$ (hr * ng/mL) | 621 |

The data showed that the compound of Example 1 had the better oral pharmacokinetic performance than that of TPX-0005, and the oral bioavailability of Example 1 reached 100%. According to the same method, all the other compounds tested also showed better PK properties profile than TPX-0005.

7. Blood-to-Brain Distribution

Male SD rats were grouped, each group having 12 rats. Each group was given the compound of Examples (10 mg/kg) by single oral gavage. The animals were fasted overnight from 10 hours before administration to 4 hours after administration. The rats were killed at 0.5, 1, 4 and 12 hours after administration, and blood and brain tissues were collected. The samples were centrifuged at 4000 rpm at 4° C. for 5 min and plasma was transferred into the centrifuge tube and stored at −80° C. until analysis. The extract from the plasma extracted by protein precipitation was analyzed by LC/MS/MS.

TABLE 6

Blood-to-brain distribution

| | TPX-0005 | | Example 1 | |
|---|---|---|---|---|
| PK parameter | Plasma | Brain | Plasma | Brain |
| $AUC_{0-inf}$ (nM · h) | 13947 | 2351 | 18163 | 20766 |
| Ratio (Brain/Plasma) | 0.17 | | 1.14 | |

Although the preferred embodiments of the present disclosure have been disclosed in order to illustrate the present disclosure, those skilled in the art should understand that various modifications, addition and replacement may be made to the present disclosure without departing from the concept and scope of the present disclosure defined by the claims.

We claim:

1. A compound of formula (1) or a pharmaceutically acceptable salt or isotope label thereof,

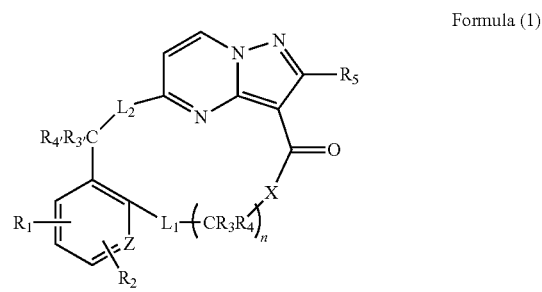

Formula (1)

wherein,

X is selected from —O—, —S— or —$CR_aR^b$—;

$R_a$ and $R_b$ are each independently selected from the following substituted or unsubstituted groups: hydrogen, halogen, a $C_{1~8}$ alkyl, a $C_{1~8}$ alkoxy, a $C_{1~8}$ haloalkyl, a $C_{3~8}$ cycloalkyl, a $C_{3~8}$ heterocyclyl, a $C_{6-20}$ aryl, a $C_{5~20}$ heteroaryl, hydroxyl, mercapto, carboxy, ester group, acyl, amino, amide, sulfonyl, cyano, or $CR_aR_b$ together forms a 3-10 membered cycloalkyl group or a 3-10 membered heterocyclic group containing at least one heteroatom;

$L_1$ is selected from —O—, —S—, —S(═O)—, —S(═O)$_2$—, —$NR_6$— or a single bond;

$L_2$ is selected from —O—, —S—, —S(═O)—, —S(═O)$_2$— or —$NR_6$—;

$R_1$, $R_2$, and $R_5$ are each independently selected from the following substituted or unsubstituted groups: hydrogen, halogen, a $C_{1~8}$ alkyl, a $C_{1~8}$ alkoxy, a $C_{1~8}$ haloalkyl, a $C_{3~8}$ cycloalkyl, a $C_{3~8}$ heterocyclic group, a $C_{6-20}$ aryl group, a $C_{5-20}$ heteroaryl group, hydroxyl, mercapto, carboxyl, ester group, acyl, amino, amide, sulfonyl or cyano;

the substituents $R_3$ and $R_4$ on each C atom are each independently selected from the following substituted or unsubstituted groups: hydrogen, halogen, a $C_{1~8}$ alkyl, a $C_{1~8}$ alkoxy, a $C_{1~8}$ haloalkyl, a $C_{3~8}$ cycloalkyl, a $C_{3~8}$ heterocyclyl, a $C_{6-20}$ aryl, a $C_{5~20}$ heteroaryl, hydroxy, mercapto, carboxy, ester group, acyl, amino, amido, sulfonyl, cyano, or the substituents $R_3$ and $R_4$ together with X group form a 3-10 membered cycloalkyl group, a 3-10 membered heterocyclic group containing at least one heteroatom, or a 5-10 membered heteroaryl group containing at least one heteroatom; or $R_3$ and $R_4$ are each independently a single bond connecting the C atom and the adjacent macrocyclic ring atom;

$R_{3'}$ and $R_{4'}$ are each independently selected from the following substituted or unsubstituted groups consisting of hydrogen, halogen, a $C_{1~8}$ alkyl, a $C_{1~8}$ alkoxy, a $C_{1~8}$ haloalkyl, a $C_{3~8}$ cycloalkyl, a $C_{3~8}$ heterocyclic group, a $C_{6-20}$ aryl group, a $C_{5-20}$ heteroaryl group, hydroxyl group, mercapto group, carboxyl group, ester group, acyl group, amino group, amide group, sulfonyl group, and cyano group;

R₆ is selected from the following substituted or unsubstituted groups: hydrogen, halogen, a $C_{1\sim8}$ alkyl, a $C_{1\sim8}$ alkoxy, a $C_{1\sim8}$ haloalkyl, a $C_{3\sim8}$ cycloalkyl, a $C_{3\sim8}$ heterocyclyl, a $C_{6\sim20}$ aryl, a $C_{5\sim20}$ heteroaryl, hydroxyl, mercapto, carboxy, ester, acyl, amino, amido, sulfonyl or cyano;

Z represents C or heteroatom as a ring atom;

n represents an integer from 1 to 10;

the substituents of the above-mentioned groups may be selected from halogen, a $C_{1\sim8}$ alkyl, a $C_{1\sim8}$ haloalkyl, a $C_{1\sim8}$ alkoxy, a $C_{3\sim8}$ cycloalkyl, a $C_{3\sim8}$ heterocyclyl, a $C_{6\sim20}$ aryl, a $C_{5\sim20}$ heteroaryl, hydroxyl, mercapto, carboxy, ester group, acyl, amino, amido, sulfonyl or cyano.

2. The compound or a pharmaceutically acceptable salt or isotope label thereof according to claim 1, wherein the compound has the structure of formula (2),

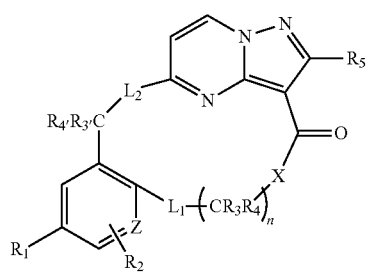

Formula (2)

wherein $R_1$ is fluorine or bromine; and/or $R_2$ is hydrogen, fluorine or bromine.

3. The compound or a pharmaceutically acceptable salt or isotope label thereof according to claim 1, wherein in Formula (1) or Formula (2), $L_1$ is selected form —O—, —S— or a single bond;

and/or $L_2$ is —NR₆—.

4. The compound or a pharmaceutically acceptable salt or isotope label thereof according to claim 1, wherein in Formula (1) or Formula (2), n represents an integer of 2, 3, 4, 5 or 6.

5. The compound or a pharmaceutically acceptable salt an or isotope label thereof according to claim 1, wherein in Formula (1) or Formula (2), the substituents $R_3$ and $R_4$ on each C atom are each independently selected from the following substituted or unsubstituted groups: hydrogen, halogen, a $C_{1\sim5}$ alkyl, a $C_{1\sim5}$ alkoxy, a $C_{1\sim5}$ haloalkyl, a $C_{3\sim6}$ cycloalkyl, or $R_3$ and $R_4$ are each independently a single bond connecting the C atom and adjacent macrocyclic ring atoms; and/or $R_{3'}$ and $R_{4'}$ are each independently selected from the following substituted or unsubstituted groups consisting of hydrogen, halogen, a $C_{1\sim5}$ alkyl, a $C_{1\sim5}$ alkoxy, a $C_{1\sim5}$ haloalkyl, and a $C_{3\sim6}$ cycloalkyl; and/or $R_5$ is selected from the following substituted or unsubstituted groups: hydrogen, halogen, a $C_{1\sim5}$ alkyl, a $C_{1\sim5}$ alkoxy, a $C_{1\sim5}$ haloalkyl, a $C_{3\sim6}$ cycloalkyl, hydroxyl, mercapto, carboxyl, amino or cyano; and/or $R_6$ is selected from the following substituted or unsubstituted groups: hydrogen, halogen, a $C_{1\sim5}$ alkyl, a $C_{1\sim5}$ alkoxy, a $C_{1\sim5}$ haloalkyl or a $C_{3\sim6}$ cycloalkyl; and/or the above substituents may be selected from fluorine, bromine, —CN, —OH, —CF₃, —NH₂, —NH($C_{1\sim4}$ alkyl), —N($C_{1\sim4}$ alkyl)₂, —CO₂$C_{1\sim4}$ alkyl, —CO₂H, —NHC(O)$C_{1\sim4}$ alkyl, —SO₂$C_{1\sim4}$ alkyl, —C(O)NH₂, —C(O)NH($C_{1\sim4}$ alkyl), —C(O)N($C_{1\sim4}$ alkyl)₂, a $C_{1\sim5}$ alkyl, a $C_{3\sim6}$ cycloalkyl, a $C_{3\sim6}$ heterocyclyl, a $C_{6\sim10}$ aryl or a $C_{5\sim10}$ heteroaryl.

6. The compound or a pharmaceutically acceptable salt or isotope label thereof according to claim 1, wherein the compound is selected from the following structures:

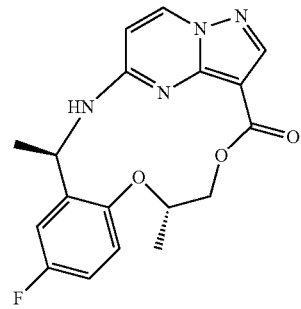

1

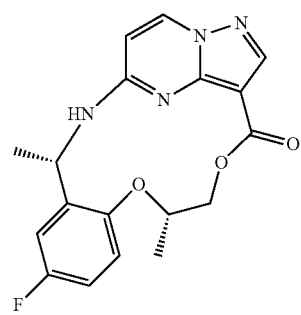

2

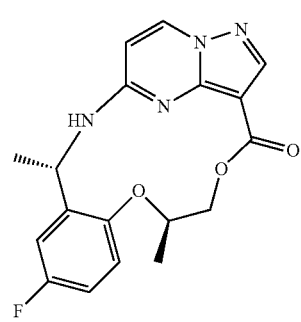

3

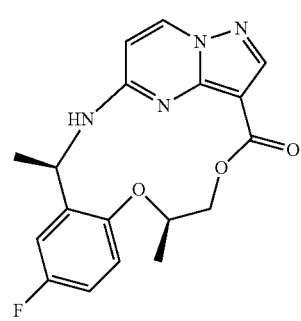

4

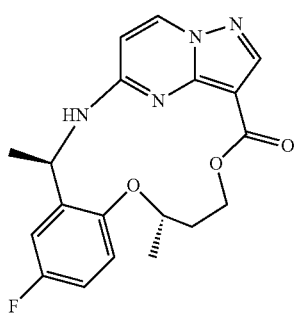
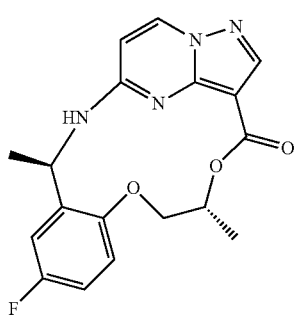
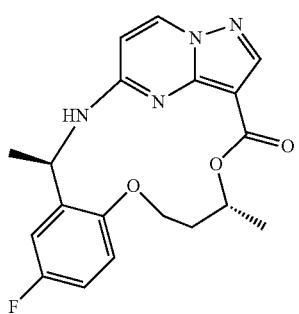
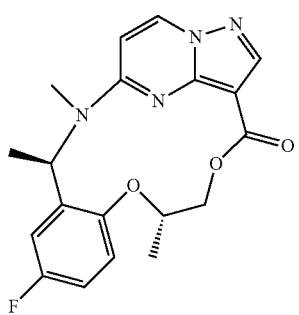
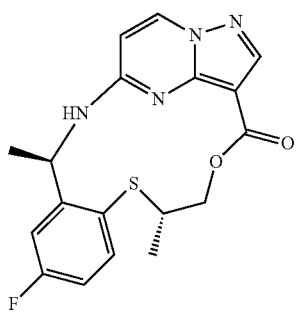
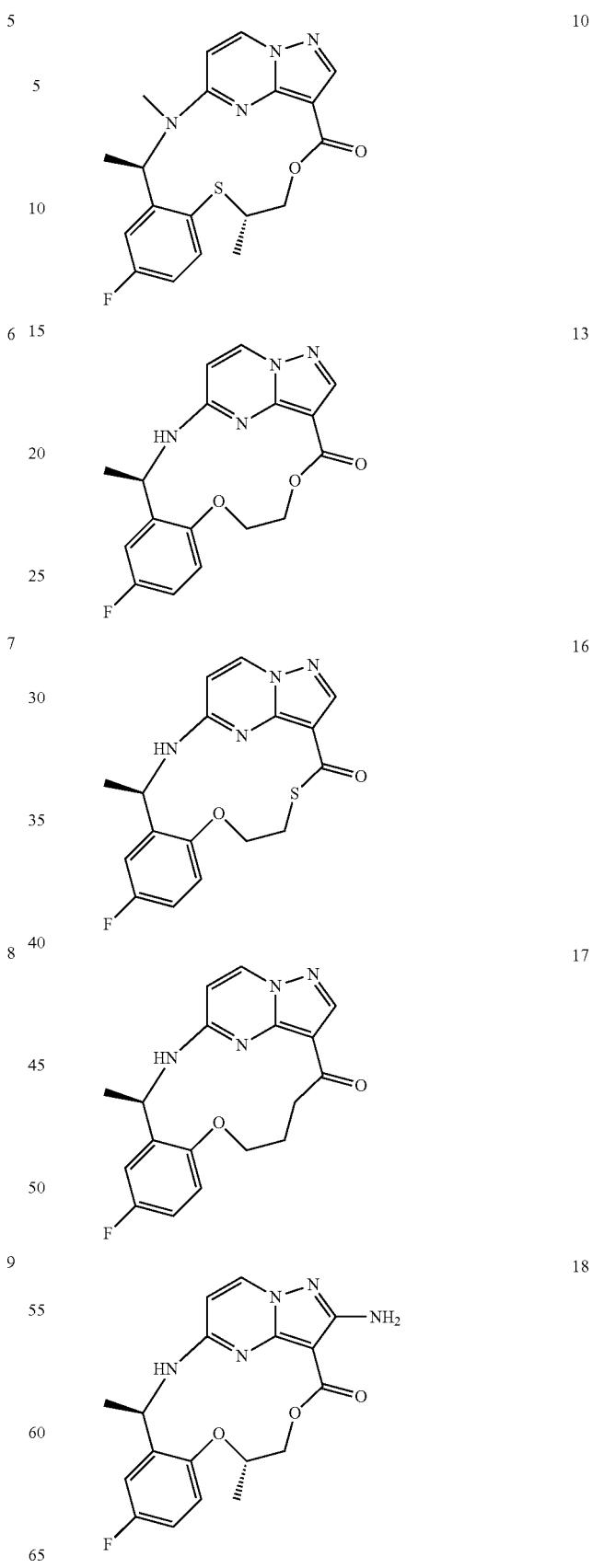

19
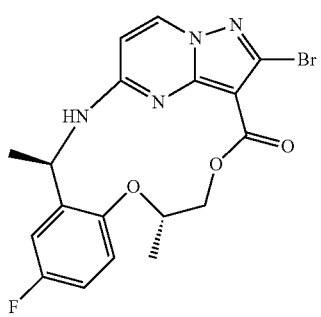
20
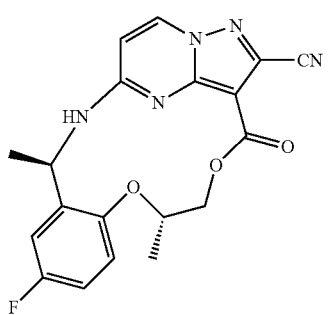
22
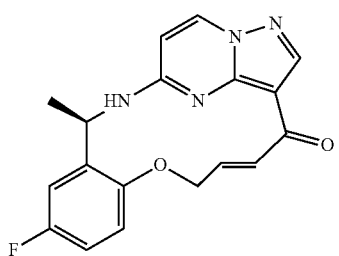
23
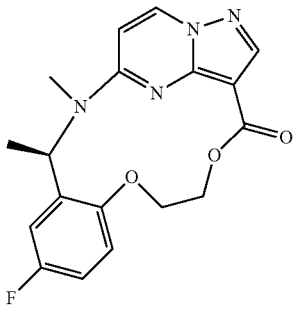
24
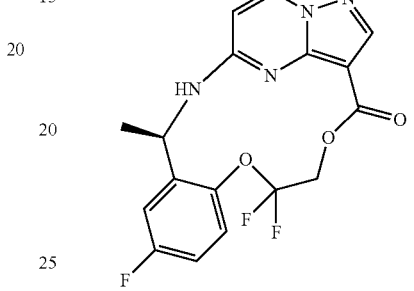
or
25
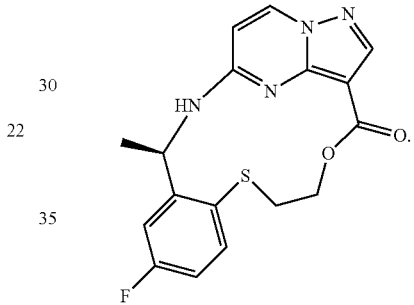
7. A pharmaceutical composition comprising the compound or a pharmaceutically acceptable salt or isotope label thereof according to claim 1, and a pharmaceutically acceptable carrier.
* * * * *